United States Patent
Hyde et al.

(10) Patent No.: US 8,527,209 B2
(45) Date of Patent: *Sep. 3, 2013

(54) REJUVENATION OR PRESERVATION OF GERM CELLS

(75) Inventors: Roderick A. Hyde, Redmond, WA (US); Edward K. Y. Jung, Bellevue, WA (US); Lowell L. Wood, Jr., Bellevue, WA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 209 days.

This patent is subject to a terminal disclaimer.

(21) Appl. No.: 12/803,447

(22) Filed: Jun. 24, 2010

(65) Prior Publication Data

US 2011/0319807 A1 Dec. 29, 2011

(51) Int. Cl.
  G06F 19/00 (2011.01)
  G06F 15/00 (2006.01)
  C12N 5/02 (2006.01)

(52) U.S. Cl.
  USPC .................................. 702/19; 700/1; 435/375

(58) Field of Classification Search
  None
  See application file for complete search history.

(56) References Cited

U.S. PATENT DOCUMENTS

| | | | |
|---|---|---|---|
| 3,921,636 A | 11/1975 | Zaffaroni | |
| 3,947,996 A | 4/1976 | Watts | |
| 5,563,059 A | 10/1996 | Alak et al. | |
| 6,300,543 B1 | 10/2001 | Cass et al. | |
| 6,673,595 B2 * | 1/2004 | Barbera-Guillem | 435/286.2 |
| 6,695,765 B1 | 2/2004 | Beebe et al. | |
| 6,789,426 B2 | 9/2004 | Yaralioglu et al. | |
| 7,010,340 B2 | 3/2006 | Scarantino et al. | |
| 7,056,529 B2 | 6/2006 | Ehringer et al. | |
| 7,540,717 B2 | 6/2009 | Sheng et al. | |
| 2003/0157086 A1 | 8/2003 | Tilly et al. | |
| 2004/0234940 A1 * | 11/2004 | Van Der Steen et al. | 435/2 |
| 2006/0019388 A1 * | 1/2006 | Hutmacher et al. | 435/394 |
| 2007/0225634 A1 * | 9/2007 | Ferren et al. | 604/27 |
| 2008/0057039 A1 | 3/2008 | Newell Rogers et al. | |
| 2008/0091119 A1 | 4/2008 | Moffitt | |
| 2008/0252459 A1 | 10/2008 | Butler et al. | |

FOREIGN PATENT DOCUMENTS

EP 0 314 937 A2 5/1989

OTHER PUBLICATIONS

Roberts et al. Culture environment modulates maturation and metabolism of human oocytes. Human Reproduction vol. 17, pp. 2950-2956 (2002).*
Naciri et al. Monitoring pH and dissolved oxygen in mammalian cell culture using optical sensors. Cytotechnology vol. 57, pp. 245-250 (2008).*
Conaghan et al. Effects of pyruvate and glucose on the development of human preimplantation embryos in vitro. Journal of Reproduction and Fertility vol. 99, pp. 87-95 (1993).*
Alahdadi et al.; "The effect of biofertilizer on soybean seed vigor and field emergence"; Journal of Food, Agriculture & Environment; Jul.-Oct. 2009; pp. 420-426; vol. 7 (3 & 4).
Brose et al.; "Creatine supplementation enhances isometric strength and body composition improvements following strength exercise training in older adults"; Abstract; 1 pg.; J Gerontol A Biol Sci Med Sci; Jan. 2003; pp. 11-19; vol. 58, No. 1.
Distelmaier et al.; "Life Cell Quantification of Mitochondrial Membrane Potential at the Single Organelle Level"; Cytometry Part A; 2008; pp. 129-138; vol. 73A; International Society for Analytical Cytology.
Erkkila et al.; "Regulation of human male germ cell death by modulators of ATP production"; Am J Physiol Endocrinol Metab; 2006; pp. E1145-E1154; vol. 290; The American Physiological Society.
Erkkila et al.; "Lactate inhibits germ cell apoptosis in the human testis"; Abstract; 1 pg.; Mol Hum Reprod; Feb. 2002; pp. 109-117; vol. 8, No. 2.
Fritz-Wolf et al.; "Structure of mitochondrial creatine kinase"; Abstract; 2 pgs.; Nature; May 23, 1996; pp. 341-345; vol. 381; Nature Publishing Group.
Grootegoed et al.; "The role of glucose, pyruvate and lactate in ATP production by rat spermatocytes and spermatids"; Abstract; 2 pgs.; Biochimica et Biophysica Acta BBA (Bioenergetics); Nov. 26, 1984; pp. 248-256; vol. 767, No. 2.
Hecht et al.; "The *Arabidopsis* Somatic Embryogenesis Receptor Kinase 1 Gene is Expressed in Developing Ovules and Embryos and Enhances Embryogenic Competence in Culture"; Plant Physiology; Nov. 2001; pp. 803-816 plus correction sheet; vol. 127; American Society of Plant Biologists.
Hitachi RFID Solutions; pp. 1-3; located at www.hitachi-eu.com/mu/Products/Mu%20Chip.html; downloaded on Mar. 5, 2010; Hitachi, Ltd.
ISSYS Integrated Sensing Systems; "Wireless, Batteryless Implantable Medical Products" pp. 1-5; located at www.niems-issys.com/implantable.shtml; downloaded on Feb. 24, 2010; ISSYS Sensing Systems, Inc.
Liang et al.; "Encapsulation of ATP into liposomes by different methods: optimization of the procedure"; J. Microencapsulation; May 2004; pp. 251-261; vol. 21, No. 3; Taylor & Francis Ltd.
Liu et al.; "A Simple and Rapid Determination of ATP, ADP and AMP Concentrations in Pericarp Tissue of Litchi Fruit by High Performance Liquid Chromatography"; Food Technol. Biotechnol.; 2006; pp. 531-534; vol. 44, No. 4.
Lunn et al.; "ATP-levels of germinating seeds in relation to vigor"; Abstract; 2 pgs.; Physiologia Plantarum; Apr. 28, 2006; pp. 164-169; vol. 53, No. 2; Physiologia Planatarum 2010.
Mayevsky et al.; "Mitochondrial function in vivo evaluated by NADH fluorescence: from animal models to human studies"; Am J Physiol Cell Physiol; 2007; pp. C615-C640; vol. 292; American Physiological Society.
McAllister et al.; "Microfabricated needles for transdermal delivery of macromolecules and nanoparticles: Fabrication methods and transport studies"; PNAS; Nov. 25, 2003; pp. 13755-13760; vol. 100, No. 24; The National Academy of Sciences of the USA.
Morohashi et al.; "ATP Synthesis in Cotyledons of Cucumber and Mung Bean Seeds during the First Hours of Imbibition"; Plant Cell Physiol.; 1988; pp. 893-896; vol. 29, No. 5; JSPP.
Nadlinger et al.; "Extracellular metabolisation of NADH by blood cells correlates with intracellular ATP levels"; Biochimica et Biophysica Acta; 2002; pp. 177-182; vol. 1573; Elsevier Science B.V.
Palmer, Biff F.; "Angiotensin-converting enzyme inhibitors and angiotensin receptor blockers: what to do if the serum creatinine and/or serum potassium concentration rises"; Nephrol Dial Transplant; 2003; pp. 1973-1975; vol. 18; European Renal Association—European Dialysis and Transplant Association.

(Continued)

Primary Examiner — John S Brusca

(57) ABSTRACT

Certain embodiments disclosed herein include, but are not limited to, at least one of compositions, methods, devices, systems, kits, or products regarding rejuvenation or preservation of germ cells or gametes. Certain embodiments disclosed herein include, but are not limited to, methods of modifying germ cells or gametes, or methods of administering modified germ cells or gametes to at least one biological tissue.

49 Claims, 14 Drawing Sheets

(56) References Cited

OTHER PUBLICATIONS

Perchec et al.; "Relationship between sperm ATP content and motility of carp spermatozoa"; Journal of Cell Science; 1995; pp. 747-753; vol. 108; The Company of Biologists Limited.

Raghavan, V.; "One Hundred Years of Zygotic Embryo Culture Investigations"; In Vitro. Cell. Dev. Biol.-Plant; Sep.-Oct. 2003; pp. 437-442; vol. 39; Society for In Vitro Biology.

Rolletschek et al.; "Evidence of a key role for photosynthetic oxygen release in oil storage in developing soybean seeds"; New Phytologist; 2005; pp. 777-786; vol. 167; New Phytologist.

Rossato et al.; "Sperm treatment with extracellular ATP increases fertilization rates in in-vitro fertilization for male factor infertility"; Human Reproduction; 1999; pp. 694-697; vol. 14, No. 3; European Society of Human Reproduction and Embryology.

Sato et al.; "Efficient Gene Delivery Into Murine Ovarian Cells by Intraovarian Injection of Plasmid DNA and Subsequent In Vivo Electroporation"; Genesis; 2003; pp. 169-174; vol. 35; Wiley-Liss, Inc.

Scaduto, Jr. et al.; "Measurement of Mitochondrial Membrane Potential Using Fluorescent Rhodamine Derivatives"; Biophysical Journal; Jan. 1999; pp. 469-477; vol. 76; Biophysical Society.

Scott et al.; "Human oocyte respiration-rate measurement—potential to improve oocyte and embryo selection?"; Reproductive BioMedicine Online; 2008; pp. 461-469; vol. 17, No. 4; Reproductive Healthcare Ltd.

Tao et al.; "Human oocyte and ovarian tissue cryopreservation and its application"; J Assist Reprod Genet; 2008; pp. 287-296; vol. 25; Springer Science + Business Media, LLC.

Tsai, Huai-Jen; "Electroporated Sperm Mediation of a Gene Transfer System for Finfish and Shellfish"; Molecular Reproduction and Development; 2000; pp. 281-284; vol. 56; Wiley-Liss, Inc.

Van Blerkom et al.; "ATP content of human oocytes and developmental potential and outcome after in-vitro fertilization and embryo transfer"; Human Reproduction; 1995; pp. 415-424; vol. 10, No. 2; Oxford University Press.

Walliman et al.; "Intracellular compartmentation, structure and function of creatine kinase isoenzymes in tissues with high and fluctuating energy demands: the 'phosphocreatine circuit' for cellular energy homeostasis"; Abstract; 1 pg.; Biochem J; Jan. 1, 1992; pp. 21-40; vol. 281, Pt. 1.

Wang et al.; "In vitro fertilization (IVF): a review of 3 decades of clinical innovation and technological advancement"; Therapeutics and Clinical Risk Management; 2006; pp. 355-364; vol. 2, No. 4; Dove Medical Press Limited.

Wang et al.; "Mitochondrial functions on oocytes and preimplantation embryos"; Journal of Zhejiang University Science B; 2009; pp. 483-492; vol. 10, No. 7.

Zhang et al.; "Deficit of mitochondria-derived ATP during oxidative stress impairs mouse MII oocyte spindles"; Cell Research; 2006; pp. 841-850; vol. 16; IBCB, SIBS, CAS.

Cavilla, J. L. et al.; "Human immature oocytes grow during culture for IVM"; Human Reproduction; Oct. 11, 2007; pp. 37-45; vol. 23, No. 1; Oxford University Press on behalf of the European Society of Human Reproduction and Embryology.

Huang, Chun-Wei et al.; "A microfluidic system for automatic cell culture" Journal of Micromechanics and Microengineering; Jun. 5, 2007; pp. 1266-2374 (plus 1 cover-page); vol. 17; IOP Publishing Ltd.

Ichikawa, Akihiko et al.; "Fluorescent Monitoring Using Microfluidics Chip and Development of Syringe Pump for Automation of Enucleation to Automate Cloning"; 2009 IEEE International Conference on Robotics and Automation; May 12-17, 2009; pp. 2231-2236; IEEE.

Kono, T. et al.; "Development of enucleated mouse oocytes reconstituted with embryonic nuclei"; Journal of Reproduction and Fertility; bearing a date of 1991; pp. 165-172; vol. 93; Journals of Reproduction & Fertility Ltd.

Marchetti, Carole et al.; "Study of mitochondrial membrane potential, reactive oxygen species, DNA fragmentation and cell viability by flow cytometry in human sperm"; bearing a date of 2002; pp. 1257-1265; vol. 17, No. 5; European Society of Human Reproduction and Embryology.

Sutton, M. L. et al.; "Effects of in-vivo and in-vitro environments on the metabolism of the cumulus-oocyte complex and its influence on oocyte developmental capacity"; Human Reproduction; bearing a date of 2003; pp. 35-48; vol. 9, No. 1; European Society of Human Reproduction and Embryology.

Wheeler, Aaron R. et al.; "Microfluidic Device for Single-Cell Analysis"; Analytical Chemistry; Jul. 15, 2003; pp. 3581-3586; vol. 75; American Chemical Society.

Chan et al.; "Expression of sperm $Ca^{2+}$-activated $K^+$ channels in *Xenopus* oocytes and their modulation by extracellular ATP"; FEBS Letters; bearing a date of 1998, received Sep. 28, 1998; pp. 177-182; vol. 438; Federation of European Biochemical Societies.

Cicirelli et al.; "Energy Metabolism and Pyridine Nucleotide Levels during *Xenopus* Oocyte Maturation"; Development Growth and Differentiation; bearing a date of 1985, received Jan. 12, 1985; pp. 283-294; vol. 27, No. 3.

Cooper, GM; "Meiosis and Fertilization"; The Cell: A Molecular Approach, $2^{nd}$ edition; bearing a date of 2000; 8 pages; Sinauer Associates; Sunderland, MA; located at: http://www.ncbi.nlm.nih.gov/books/NBK9901/.

Dashwood et al.; "Chemopreventive properties of chlorophylls towards aflatoxin $B_1$ : a review of the antimutagenicity and anticarcinogenicity data in rainbow trout"; Carcinogenesis; bearing a date of Oct. 1999; pp. 1-11 (1919-1926); vol. 20, No. 10; NIH Public Access.

Gilbert, SF; "Early Development in Fish"; Developmental Biology, $6^{th}$ edition; bearing a date of 2000; pp. 1-6; Sinauer Associates; Sunderland, MA; located at: http://www.ncbi.nlm.nih.gov/books/NBK10100/.

Gilbert, SF; "Oogenesis"; Developmental Biology, $6^{th}$ edition; bearing a date of 2000; pp. 1-9; Sinauer Associates; Sunderland, MA; located at: http://www.ncbi.nlm.nih.gov/books/NBK10008/.

Grant et al.; "Receptor-mediated Endocytosis in the *Caenorhabditis elegans* Oocyte"; Molecular Biology of the Cell; bearing a date of Dec. 1999; pp. 4311-4326; vol. 10; The American Society for Cell Biology.

Greenstein, David; "Control of oocyte meiotic maturation and fertilization"; *WormBook*, ed., The *C. elegans* Research Community; bearing a date of 2005, published Dec. 28, 2005; pp. 1-11; Wormbook.org; located at: http://wormbook.org/chapters/www_controloocytematuration/controloocytematuration.html.

Imamura et al.; "Visualization of ATP levels inside single living cells with fluorescence resonance energy transfer-based genetically encoded indicators"; PNAS; bearing a date of Sep. 15, 2009; pp. 15651-15656; vol. 106, No. 37.

Minshull et al.; "*Xenopus* oocyte maturation does not require new cyclin synthesis"; J Cell Biol.; bearing a date of Aug. 1991; 1 page, Abstract Only; vol. 114, No. 4; located at: http://www.ncbi.nlm.nih.gov/pubmed/1651338.

Mulner et al.; "Cyclic Amp Synthesis in *Xenopus laevis* Oocytes Inhibition by Progesterone"; Biochimica et Biophysica Acta; bearing a date of 1979, received Oct. 2, 1978; pp. 179-184; Elsevier/North-Holland Biomedical Press.

Opresko et al.; "Receptor-Mediated Endocytosis in *Xenopus* Oocytes"; The Journal of Biological Chemistry; bearing a date of 1987, received for publication Apr. 29, 1986; pp. 4109-4115; vol. 262, No. 9, Issue of Mar. 25; The American Society of Biological Chemists, Inc.

Van Blerkom et al.; "Inner Mitochondrial Membrane Potential ($\Delta\Psi m$), Cytoplasmic ATP Content and Free $Ca^{2+}$ Levels in Metaphase II Mouse Oocytes"; Human Reproduction; bearing a date of 2003, submitted Mar. 31, 2003; pp. 2429-2440; vol. 18, No. 11; European Society of Human Reproduction and Embryology.

Van Blerkom, Jonathan.; "Occurrence and Developmental Consequences of Aberrant Cellular Organization in Meiotically Mature Human Oocytes After Exogenous Ovarian Hyperstimulation"; Journal of Electron Microscopy Technique; bearing a date of 1990, received Jun. 15, 1989; pp. 324-346; vol. 16; Wiley-Liss, Inc.

Wasserman et al.; "The Maturation Response of Stage IV, V, and VI *Xenopus* oocytes to progesterone stimulation in vitro"; Developmental Biology; bearing a date of Oct. 1984; pp. 1-3, Abstract Only; vol. 105, Issue 2; Elsevier Inc.

Wrobel et al.; "Fusion of Cationic Liposomes with Mammalian Cells Occurs After Endocytosis"; Biochimica et Biophysica Acta; bearing a date of 1995, received Oct. 7, 1994; pp. 296-304; vol. 1235; Elsevier Science B.V.

Baker et al.; "A Continuous, Implantable Lactate Sensor"; Analytical Chemistry; bearing a date of May 1, 1995; pp. 1536-1540; vol. 67, No. 9; American Chemical Society.

Choi et al.; "An Integrated Microfluidic Biochemical Detection System for Protein Analysis with Magnetic Bead-Based Sampling Capabilities"; Lab Chip; bearing a date of 2002, accepted Nov. 2, 2001; pp. 27-30; vol. 2; The Royal Journal of Chemistry 2002.

Mitrelias et al.; "Magnetic Devices for Ultra High Throughput Biological Analysis"; NSTI-Nanotech 2006; bearing a date of 2006; pp. 256-259; vol. 2.

González et al.; "Leptin and Leptin Receptor are Expressed in the Human Endometrium and Endometrial Leptin Secretion is Regulated by the Human Blastocyst"; The Journal of Clinical Endocrinology & Metabolism; bearing a date of 2000, accepted Sep. 6, 2000; pp. 4883-4888; vol. 85, No. 12; The Endocrine Society; U.S.A.

* cited by examiner

FIG. 1

100 A delivery device comprising:

110 a housing including at least one reservoir containing at least one composition including at least one exogenous energy supplying factor; the reservoir configured to receive, retain, and dispense at least a portion of the composition to at least one reproductive cell or tissue 115 wherein the delivery device is implantable 120 wherein the at least one composition further includes at least one pharmaceutically-acceptable carrier or excipient 130 wherein the housing includes one or more ports 140 wherein at least one of the one or more ports includes at least one outlet port or at least one inlet port 150 further comprising one or more controllable output mechanisms operably linked to the one or more ports to control dispensing of at least a portion of the composition from the at least one reservoir 155 wherein the at least one controllable output mechanism includes at least one of a micropump, valve, or actuator 170 wherein the actuator includes at least one of a piezoelectric actuator, electrostatic actuator, thermal actuator, shape-memory alloy actuator, bioactuator, or magnetic actuator 160 wherein the valve includes at least one of a one-way valve, or pressure settable valve 175 wherein the at least one controllable output mechanism includes at least one thermal or nonthermal gate in communication with the at least one outlet port of the at least one reservoir

FIG. 4

400 wherein the at least one detection material includes at least one of a radioactive, luminescent, colorimetric, fluorescent, or odorous substance 410 wherein the at least one detection material includes at least one of a taggant, contrast agent, or electronic identification device 420 wherein the at least one electronic identification device includes at least one radio frequency identification device 430 further comprising at least one sensor 440 wherein the at least one sensor is configured to receive information associated with at least one of temperature, pH, inflammation, presence of at least one substance, detection material, or biological response to administration of the composition 450 further comprising a controller configured to respond to the at least one sensor.

460 wherein the at least one detection material includes at least one of a diamagnetic particle, ferromagnetic particle, paramagnetic particle, super paramagnetic particle, particle with altered isotope, or other magnetic particle 470 wherein the at least one detection material is responsive to at least one of the presence or level of the composition; or the presence or level of at least one reproductive cell or substance associated with the dispensing of the composition 480 wherein the at least one detection material is responsive to the approximate quantity of at least one of the composition, or at least one reproductive cell or substance associated with the release of the composition

FIG. 5

500 wherein the at least one detection material is responsive to at least one of: enzyme, acid, amino acid, peptide, polypeptide, protein, oligonucleotide, nucleic acid, ribonucleic acid, oligosaccharide, polysaccharide, glycopeptide, glycolipid, lipoprotein, sphingolipid, glycosphingolipid, glycoprotein, peptidoglycan, lipid, carbohydrate, metalloprotein, proteoglycan, chromosome, adhesion molecule, cytokine, chemokine, immunoglobulin, antibody, antigen, platelet, extracellular matrix, blood plasma, cell wall, hormone, organic compound, inorganic compound, salt, or cell ligand 510 wherein the at least one detection material is responsive to at least one of: glucose, lactate, urea, uric acid, glycogen, oxygen, carbon dioxide, carbon monoxide, ketone, nitric oxide, nitrous oxide, alcohol, alkaloid, pH, albumin, ATP, NADH, $FADH_2$, pyruvate, creatinine, cholesterol, alpha-fetoprotein, chorionic gonadotropin, estrogen, progesterone, testosterone, thyroxine, melatonin, calcitonin, antimullerian hormone, angiotensin, follicle-stimulating hormone, gonadotropin-releasing hormone, mitochondria, growth hormone, growth hormone-releasing hormone, insulin, human placental lactogen, oxytocin, luteinizing hormone, prolactin, cortisol, aldosterone, estradiol, estriol, estrone, leukotriene, vitamin, mineral, renin, DHEA, DHT, alloisoleucine, or a precursor of any thereof 520 further comprising at least one memory mechanism for storing instructions for generating and transmitting an electromagnetic control signal 530 further comprising at least one imaging apparatus capable of imaging the approximate quantity within a treatment region relating to at least one of the composition; at least one reproductive cell, or at least one substance associated with dispensing the composition 540 further comprising at least one memory location for recording information related to sensing information, imaging information, transmitting information, or other information related to the delivery device 550 wherein the at least one memory location is configured to record information regarding at least one sensor 560 wherein the at least one memory location is configured to record information regarding at least one of a sensed condition, history, or performance of the device

FIG. 6

600 wherein the at least one memory location is configured to record information regarding one or more of the date, time, presence or approximate quantity of at least one of the administered composition, or at least one reproductive cell or substance associated with the dispensing of the composition 610 wherein the at least one reproductive cell or substance associated with dispensing of the composition includes at least one of an organic or inorganic small molecule, nucleic acid, amino acid, peptide, polypeptide, protein, glycopeptide, glycoprotein, glycolipid, lipopolysaccharide, peptidoglycan, proteoglycan, lipid, lipoprotein, glycosphingolipid, metalloprotein, liposome, chromosome, nucleus, acid, base, buffer, protic solvent, aprotic solvent, carbohydrate, ATP, creatine, lactate, phosphocreatine, pyruvate, glucose, lipopolysaccharide, vitamin, mineral, cytokine, chemokine, antibody, element, hormone, virus, enzyme, oligonucleotide, ribonucleic acid, oligosaccharide, polysaccharide, adhesion molecule, NADH, FADH$_2$, estrogen, progesterone, testosterone, thyroxine, corticotrophin-releasing hormone, follicle-stimulating hormone, gonadotropin-releasing hormone, growth hormone, growth hormone-releasing hormone, insulin, oxytocin, luteinizing hormone, leptin, prolactin, cortisol, aldosterone, estradiol, estriol, estrone, DHEA, DHT, germ cell, gametegonium, gamete, or reproductive supporting cell. In an embodiment, the reproductive cell includes but is not limited to at least one oogonium, primary oocyte, secondary oocyte, ootid, ovum, polar body, follicular cell, granulosa cell, cumulus cell, spermatogonia, primary spermatocyte, secondary spermatocyte, spermatid, spermatozoa, Sertoli cell, or Leydig cell 620 further comprising at least one information transmission mechanism configured to transmit information recorded by the at least one electronic memory location 630 wherein the device is located in or is substantially in the form of one or more of a spray apparatus, pump apparatus, bioreactor, or drilling apparatus 640 wherein the device is substantially in the form of one or more of a patch, oral inhaler, nasal spray or other orifice spray, iontophoretic apparatus, oral consumable, ocular or otic dropper or spray, stent, shunt, orifice insert, ductal implant, organ implant, orifice spray or inhaler, sutures, surgical staples, bandages, micro-electromechanical device, nano-electromechanical device, or absorbable mesh 650 further comprising one or more inlet mechanisms for receiving external delivery of the at least one composition

FIG. 9

900 further comprising one or more instructions for determining one or more parameters for selecting the at least one reproductive cell from other reproductive cells 910 further comprising one or more instructions for determining one or more parameters for administering the composition to at least one reproductive cell 920 further comprising one or more instructions for receiving information related to one or more reproductive cell indicators prior to, during, or subsequent to administering the composition to the at least one reproductive cell 930 wherein the information related to one or more reproductive cell indicators includes information from at least one of an assay, image, or gross assessment of the at least one reproductive cell or reproductive cell related tissue prior to, during, or subsequent to administering the composition 940 wherein the assay includes at least one technique including spectroscopy, microscopy, electrochemical detection, polynucleotide detection, histological examination, biopsy analysis, fluorescence resonance energy transfer, electron transfer, enzyme assay, electrical conductivity, isoelectric focusing, chromatography, immunoprecipitation, immunoseparation, aptamer binding, filtration, electrophoresis, immunoassay, or radioactive assay 950 wherein the at least one image includes one or more images acquired by at least one of laser, holography, x-ray crystallography, optical coherence tomography, computer-assisted tomography scan, computed tomography, magnetic resonance imaging, positron-emission tomography scan, ultrasound, x-ray, electrical-impedance monitoring, microscopy, spectrometry, flow cytometry, radioisotope imaging, thermal imaging, infrared visualization, multiphoton calcium-imaging, photography, or *in silico* generation

FIG. 11

1100 A computer program product, comprising:

1110 a recordable medium bearing one or more instructions for regulating dispensing of at least one delivery device to at least one reproductive cell, wherein the delivery device includes a composition including at least one exogenous energy supplying factor, and generating at least one output 1120 wherein the recordable medium includes a computer-readable medium 1130 wherein the recordable medium includes a communications medium 1140 further comprising one or more instructions for receiving information related to one or more reproductive cell indicators prior to, during, or subsequent to administering the composition 1160 wherein the output includes at least one protocol for making the composition 1170 wherein the output includes at least one protocol for administering the composition to at least one reproductive cell 1180 wherein the output includes at least one graphical illustration of one or more of the composition, or at least one reproductive cell or substance associated with the at least one reproductive cell, at least one property of the at least one delivery device, or at least one property of dispensing the at least one delivery device 1190 further comprising one or more instructions for displaying results of the processing

FIG. 12

1200 A computer-implemented method, comprising:

1210 regulating dispensing at least one composition from at least one delivery device to at least one reproductive cell, the composition including at least one energy supplying factor 1220 wherein the at least one delivery device includes at least one implantable delivery device 1230 further comprising generating at least one output 1240 wherein the generating at least one output includes generating at least one output to a user 1250 wherein the user includes at least one entity 1260 wherein the entity includes at least one person, or computer 1270 wherein the at least one output includes at least one graphical illustration of one or more of the composition, or at least one reproductive cell or substance associated with the at least one reproductive cell; at least one property of the at least one delivery device; or at least one property of dispensing the at least one delivery device 1280 wherein the at least one output includes at least one protocol for making the composition based on one or more parameters of the at least one reproductive cell 1285 wherein the at least one output includes one or more parameters for selecting the at least one reproductive cell from other reproductive cells

FIG. 13

1300 wherein the at least one output includes at least one protocol for dispensing the at least one composition to the at least one reproductive cell 1302 wherein the dispensing the at least one composition to the at least one reproductive cell includes dispensing the at least one composition in response to one or more reproductive cell indicators 1305 wherein the at least one output includes at least one output to a user readable display 1308 wherein the user readable display includes a human readable display 1310 wherein the user readable display includes one or more active displays 1320 wherein the user readable display includes one or more passive displays 1330 wherein the user readable display includes one or more of a numeric format, graphical format, or audio format 1340 further comprising receiving information related to one or more reproductive cell indicators prior to, during, or subsequent to administering the composition to the at least one reproductive cell 1350 wherein the receiving information related to one or more reproductive cell indicators includes information from at least one of an assay, image, or gross assessment of the at least one biological tissue prior to, during, or subsequent to administering the composition

FIG. 14

1400 wherein the assay includes at least one technique including spectroscopy, microscopy, electrochemical detection, polynucleotide detection, histological examination, biopsy analysis, fluorescence resonance energy transfer, electron transfer, enzyme assay, electrical conductivity, isoelectric focusing, chromatography, immunoprecipitation, immunoseparation, aptamer binding, filtration, electrophoresis, immunoassay, or radioactive assay 1420 wherein the at least one image includes one or more images acquired by at least one of laser, holography, x-ray crystallography, optical coherence tomography, computer-assisted tomography scan, computed tomography, magnetic resonance imaging, positron-emission tomography scan, ultrasound, x-ray, electrical-impedance monitoring, microscopy, spectrometry, flow cytometry, radioisotope imaging, thermal imaging, infrared visualization, multiphoton calcium-imaging, photography, or *in silico* generation 1440 wherein the at least one reproductive cell is located in at least one of *in situ, in vitro, in vivo, in utero, in planta, in silico,* or *ex vivo*

1450 wherein the at least one reproductive cell is at least partially located in at least one subject 1460 wherein the at least one subject includes at least one of an invertebrate or vertebrate animal 1470 wherein the at least one subject includes at least one of a reptile, mammal, amphibian, bird, or fish 1480 wherein the at least one subject includes at least one human 1490 wherein the at least one subject includes at least one plant

REJUVENATION OR PRESERVATION OF GERM CELLS

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)). All subject matter of the Related Applications and of any and all parent, grandparent, great-grandparent, etc. applications of the Related Applications is incorporated herein by reference to the extent such subject matter is not inconsistent herewith.

RELATED APPLICATIONS

For purposes of the USPTO extra-statutory requirements, the present application is related to U.S. patent application Ser. No. 12/803,450, entitled REJUVENATION OR PRESERVATION OF GERM CELLS, naming Roderick A. Hyde, Edward K.Y. Jung and Lowell L. Wood, Jr. as inventors, filed 24 Jun. 2010, which is currently co-pending, or is an application of which a currently co-pending application is entitled to the benefit of the filing date.

For purposes of the USPTO extra-statutory requirements, the present application is related to U.S. patent application Ser. No. 12/803,448, entitled REJUVENATION OR PRESERVATION OF GERM CELLS, naming Roderick A. Hyde, Edward K.Y. Jung and Lowell L. Wood, Jr. as inventors, filed 24 Jun. 2010, which is currently co-pending, or is an application of which a currently co-pending application is entitled to the benefit of the filing date.

For purposes of the USPTO extra-statutory requirements, the present application is related to U.S. patent application Ser. No. 12/803,446, entitled REJUVENATION OR PRESERVATION OF GERM CELLS, naming Roderick A. Hyde, Edward K.Y. Jung and Lowell L. Wood, Jr. as inventors, filed 24 Jun. 2010, which is currently co-pending, or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation or continuation-in-part. Stephen G. Kunin, *Benefit of Prior-Filed Application*, USPTO Official Gazette Mar. 18, 2003. The present Applicant Entity (hereinafter "Applicant") has provided above a specific reference to the application(s)from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s).

All subject matter of the Related Applications and of any and all parent, grandparent, great-grandparent, etc. applications of the Related Applications is incorporated herein by reference to the extent such subject matter is not inconsistent herewith.

SUMMARY

Disclosed herein include embodiments relating to compositions, methods, delivery devices, computer systems, program products, and computer-implemented methods related to modified reproductive cells. In an embodiment, a method of modifying a reproductive cell comprises actively introducing at least one exogenous energy supplying factor into at least one intracellular compartment of a reproductive cell. In an embodiment, a method of restoring mitochondrial function in a reproductive cell comprises administering to a subject containing at least one reproductive cell, an amount and for a time sufficient to increase endogenous ATP levels of at least one of the subject's reproductive cells, of at least one of an angiotensin receptor blocker or an angiotensin converting enzyme inhibitor. In an embodiment, the angiotensin receptor inhibitor includes angiotensin-II receptor blocker (ARB).

In an embodiment, a method of modifying a reproductive cell comprises providing at least one of creatine, phosphorcreatine, or creatine kinase to a reproductive cell. In an embodiment, the reproductive cell is located in a subject. In an embodiment, a method for up-regulating mitochondrial function in a reproductive cell comprises actively introducing at least one exogenous energy supplying factor into at least one intracellular compartment of a reproductive cell.

In an embodiment, a method of modifying an oocyte comprises introducing at least one exogenous energy supplying factor into at least one intracellular compartment of an oocyte. In an embodiment, the introducing at least one exogenous energy supplying factor includes allowing at least one exogenous energy supply factor to diffuse into the at least one intracellular compartment of the oocyte. In an embodiment, the introducing at least one exogenous energy supplying factor includes liposomal introduction by way of endocytosis.

In an embodiment, a method of modifying a female reproductive cell comprises introducing at least one exogenous energy supplying factor into at least one intracellular compartment of a female reproductive cell. In an embodiment, the female reproductive cell includes at least one of an oogonium, primary oocyte, secondary oocyte, ootid, ovum, polar body, follicular cell, or cumulus cell.

In an embodiment, a method of modifying a reproductive cell comprises introducing at least one exogenous constituent into at least one intracellular compartment of a reproductive cell, the exogenous constituent configured to increase at least one endogenous energy supplying factor.

In an embodiment, a method of selecting at least one reproductive cell comprises detecting at least one endogenous energy supplying factor in at least one reproductive cell, and scoring the at least one reproductive cell based on the detection.

In an embodiment, a modified reproductive cell is produced by the process of actively introducing at least one exogenous energy supplying factor into at least one intracellular compartment of a reproductive cell.

In an embodiment, a kit comprises a detection material responsive to at least one reproductive cell indicator, and means for administering at least one exogenous energy supplying factor to at least one reproductive cell.

In an embodiment, a delivery device comprises a housing including at least one reservoir containing at least one composition including at least one exogenous energy supplying factor; the reservoir configured to receive, retain, and dispense at least a portion of the composition to at least one reproductive cell or tissue.

In an embodiment, a system comprises at least one computing device; at least one delivery device configured to receive, retain and dispense at least a portion of a composition including at least one energy supplying factor to at least one reproductive cell; and a recordable medium including one or more instructions that when executed on the computing device cause the computing device to regulate dispensing of at least a portion of the composition.

In an embodiment, a computer program product comprises a recordable medium bearing one or more instructions for regulating dispensing of at least one delivery device to at least one reproductive cell, wherein the delivery device includes a composition including at least one exogenous energy supplying factor, and generating at least one output.

In an embodiment, a computer-implemented method comprises regulating dispensing a composition from at least one delivery device to at least one reproductive cell, the composition including at least one energy supplying factor.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIG. 1 illustrates a partial view of a particular embodiment of a delivery device disclosed herein.

FIG. 4 illustrates a partial view of various embodiments of the device of FIG. 1.

FIG. 5 illustrates a partial view of various embodiments of the device of FIG. 1.

FIG. 6 illustrates a partial view of various embodiments of the device of FIG. 1.

FIG. 9 illustrates a partial view of various embodiments of the system of FIG. 7.

FIG. 11 illustrates a partial view of a particular embodiment of a computer program product disclosed herein.

FIG. 12 illustrates a partial view of a particular embodiment of a computer-implemented method disclosed herein.

FIG. 13 illustrates a partial view of a particular embodiment of the computer-implemented method of FIG. 12.

FIG. 14 illustrates a partial view of a particular embodiment of the computer-implemented method of FIG. 12.

DETAILED DESCRIPTION

Figure 2:
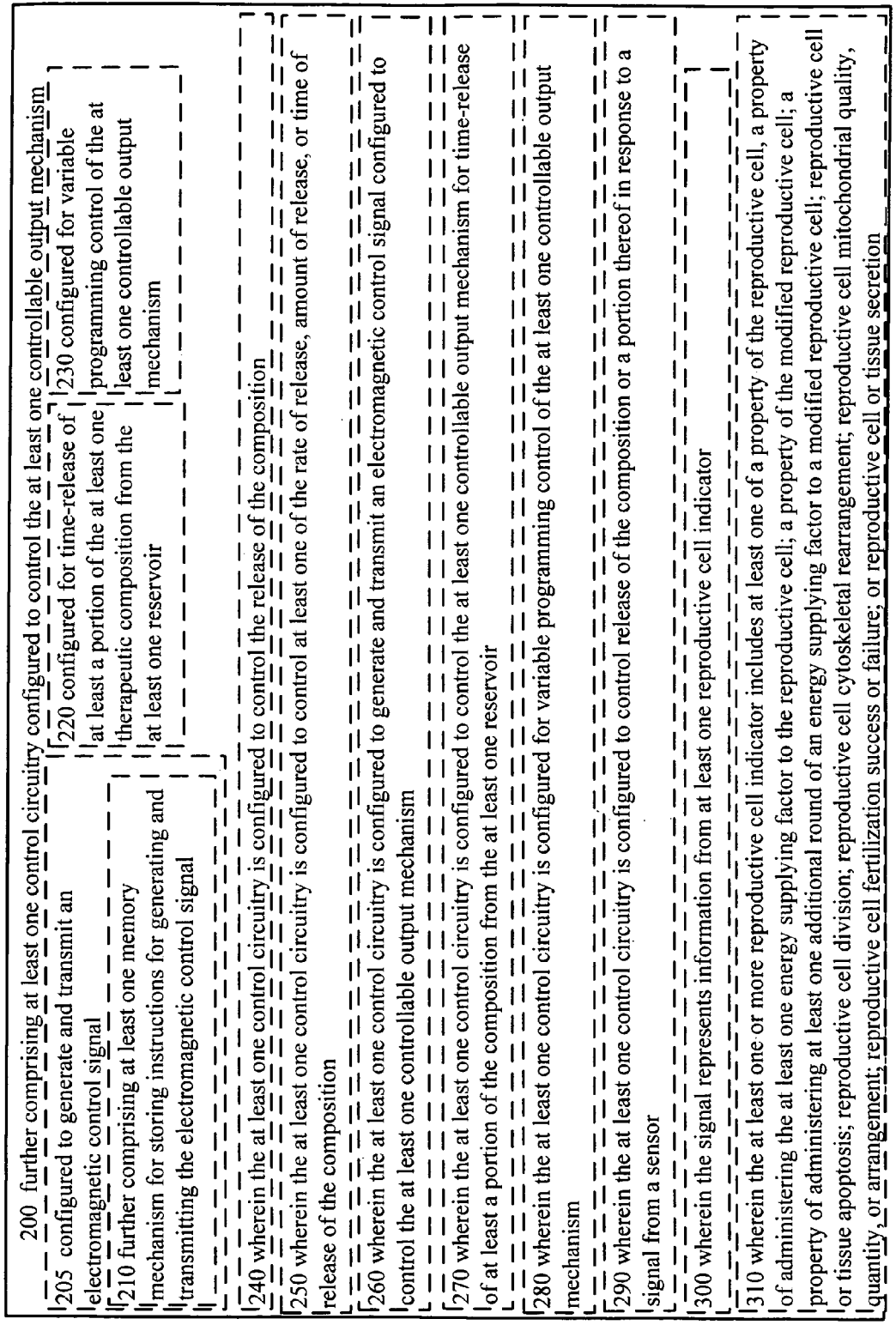
FIG. 2 illustrates a partial view of various embodiments of the device of FIG. 1.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

In most animal species, gametogenesis occurs directly through meiosis in the gonads, following migration of primordial germ cells during early development. The cells, gametogonium, then pass through various stages of development, from primary gametocytes, to secondary gametocytes, to gametid, and finally to gametes.

Gametogenesis in plants occurs by mitosis in gametophytes that grow from haploid spores after sporic meiosis. The male plant gamete is produced inside the pollen grain, while the female gamete is produced inside the embryo sac of the ovule.

Rejuvenation or preservation of vigorous reproductive cells (for example, germ cells, any of the various stages of gametogonium, as well as the corresponding reproductive supporting cells) increases the rate of fertilization, implantation, or birth of viable offspring. For example, mammalian oocyte and sperm vigor or quality is considered to be the main limiting factor for in vitro fertilization (IVF) procedures. (See, e.g., Wang, et al., J. Zhejiang *Univ. Sci. B*, vol. 10(7), pp. 483-492 (2009); and Rossato, et al., *Human Rep.* vol. 14, no. 3, pp. 694-697 (1999), each of which is incorporated herein by reference).

Reproductive cell vigor decreases with increasing age of the subject, as well as with increasing duration ex vivo storage (for example, when harvested for in vitro fertilization procedures). It is reported that poor reproductive cell quality or vigor corresponds to an increase in age-related dysfunctions, such as a decrease in mitochondrial membrane potential, increase in mitochondrial DNA (mtDNA) damage, increase in chromosomal aneuploidy, increase in the incidence of apoptosis, and changes in mitochondrial gene expression. Id. It is further reported that any of these dysfunctions can cause developmental retardation or arrest of preimplantation embryos in mammals. Id.

According to published reports, the oxidative phosphorylation within mitochondria provides a major source of ATP needed for energy by mature gametes. See, for example, Zhang, et al. *Cell Res.* vol. 16, pp. 841-850 (2006), and Wang, et al. *J. Zhejiang Univ. Sci. B*, Ibid.; each of which is incorporated herein by reference. It has been reported that a deficit of mitochondria-derived ATP impairs mammalian oocyte spindles during mitosis, thereby contributing to developmental problems in the developing embryo. See, e.g., Zhang, et al. Ibid.

In relation to ATP levels, it has been reported that spermatozoa motility is directly correlated to ATP levels synthesized by mitochondrial respiration and stored prior to activation. See, for example, Perchec, et al., *J. Cell Sci.*, vol. 108, pp. 747-753 (1995), which is incorporated herein by reference. It has also been reported that ATP levels decline with time during storage of spermatazoan cells. See, for example, *Rep. Biol.* vol. 9, no. 1, pp. 39-49 (2009). Finally, exogenous lactate has been reported to serve as an energy supply for mitochondria, as it supports ATP production by gametes, particularly in regard to spermatocytes, spermatids, and spermatogonia. See, for example, Erkkila, et al. *Mol. Hum. Reprod.* Abstract Vol. 8, pp. 109-117, (2002); and Grootegoed, et al. *Biochim. et Biophys. Acta*, vol. 767, No. 2, pp. 248-256 (1984), each of which is incorporated herein by reference.

It has been reported that the mitochondrial intermembrane space includes creatine kinase, an enzyme that produces phosphor-creatine from ATP and creatine. See, e.g., Wallimann, et al., *Biochem. J.* vol. 281, pp. 21-40 (1992), which is incorporated herein by reference. As has been reported, creatine kinase is an enzyme utilized for energy metabolism by catalyzing the reversible transfer of a phosphoryl group from phosphocreatine to ADP, making the creatine pathway critical for increasing or maintaining the vigor of reproductive cells. See, e.g., Fritz-Wolf, et al. Abstract, *Nature* vol. 381, pp. 341-345 (1996), which is incorporated herein by reference.

In plants, ATP-levels of germinating seeds are reported to be correlative to vigor. For example, under conditions of artificial aging, seed deterioration was reflected in ATP-levels long before loss of viability could be detected by conventional germination tests. See, for example, Lunn and Madsen, *Physiol. Plant.*, vol. 53, no. 2, pp. 164-169 (2006), which is incorporated herein by reference.

It has been reported that oocyte communication with the surrounding cumulus cells is also an important indicator for oocyte development. Id. The cumulus cells are responsible for nutrition supply of oocytes in the final phase of oocyte maturation. Morphological characters of cumulus cells can be used to value oocyte quality and its maturation. Id. For example, compact and complete cumulus and bright and homogenous ooplasm are considered indicators of high-quality immature oocytes, while cumulus cells with no more than three layers or dark and heterogeneous ooplasm indicates low-quality immature oocytes. Id.

In general, it is reported that during meiotic progression, oocyte maturation is linked with cumulus expansion or apoptosis and the number of cumulus cells attached to matured oocytes decreases with age. Id. It is reported that mitochondrial redistribution and their oxidative activity are essential to the degree of cumulus cell apoptosis during oocyte maturation. Id. Thus, mitochondria play a role in the reproductive supporting cells, as well as the developing gametogonium itself The mitochondrial DNA content in oocytes with normal fertilization rate is reportedly higher than that in abnormal oocytes, and aging of the subject from which the oocytes originate has been reported to exert a negative influence on the process of mitochondriogenesis. Id. In mammalian oocytes, mitochondria reportedly regulate calcium and synthesize ATP, both of which are necessary for good quality oocytes. Id. This contributes to the decline of the vigor of the oocytes with increasing age in animal subjects.

Likewise, in spermatogenesis, male germ cell death is reported to be modulated by ATP production, particularly by the mitochondria in the maturing gamete cells as well as the supporting Sertoli cells. See, for example, Erkkila, et al., *Am. J. Physiol. Endocrinol. Metab.* vol. 290, pp. E1145-E1154 (2006), which is incorporated herein by reference.

Thus, in an embodiment disclosed herein, increasing intracellular levels of an energy supplying factor is conducive to the preservation or restoration of characteristics of reproductive cells that are typically found in healthy, young-aged subjects. In some instances, such characteristics have declined, for example, due to age, illness, genetic disorder, mitochondrial defect, or other causes.

In an embodiment, at least one energy supplying factor (such as ATP, creatine, lactate, etc.) is provided to a reproductive cell, which increases the intracellular levels of the energy supplying factor (e.g., ATP). In an embodiment, the at least one energy supplying factor is delivered to the environment or microenvironment of the reproductive cell. In an embodiment, the at least one energy supplying factor is intracellularly delivered to the reproductive cell.

For example, methods of modifying at least one reproductive cell include introducing at least one exogenous energy supplying factor into at least one intracellular compartment of a reproductive cell. In an embodiment, the introducing the at least one exogenous energy supplying factor includes actively or passively introducing the at least one exogenous energy supplying factor.

In an embodiment, the actively introducing at least one exogenous energy supplying factor into at least one intracellular compartment of a reproductive cell includes injecting or electroporating the reproductive cell.

As indicated herein, the at least one exogenous energy supplying factor includes, but is not limited to, at least one of exogenous creatine, exogenous phosphocreatine, exogenous creatine kinase, exogenous chlorophyll, exogenous lactate, exogenous glucose or other carbohydrate, exogenous calcium, exogenous ATP, exogenous ADP, exogenous AMP, or a precursor thereof.

In an embodiment, the intracellular compartment of a reproductive cell includes at least one of a nucleolus, nucleus, ribosome, vesicle, rough endoplasmic reticulum, Golgi apparatus, cytoskeleton, smooth endoplasmic reticulum, mitochondria, vacuole, cytoplasm, lysosome, or centriole. In an embodiment, the reproductive cell is located in at least one of in situ, in vitro, in vivo, in utero, in planta, in silico, or ex vivo.

In an embodiment, a method of modifying at least one reproductive cell includes detecting at least one endogenous energy supplying factor in the reproductive cell prior to delivering at least one exogenous energy supplying factor thereto. In an embodiment, the at least one endogenous energy supplying factor is the same factor as the exogenous energy supplying factor. In an embodiment, a method of modifying at least one reproductive cell includes measuring at least one endogenous energy supplying factor in the reproductive cell subsequent to injecting at least one exogenous energy supplying factor therein.

In an embodiment, the at least one exogenous energy supplying factor is injected in response to the presence or level of at least one endogenous energy supplying factor in the reproductive cell. In an embodiment, a method of modifying the at least one reproductive cell includes detecting or measuring the level of the at least one exogenous energy supplying factor in the reproductive cell. In an embodiment, the at least one exogenous energy supplying factor is provided in response to the presence or level of at least one exogenous energy supplying factor previously delivered to the reproductive cell. In an embodiment, the at least one exogenous energy supplying factor is provided in response to the presence or level of at least one reproductive cell indicator. In an embodiment, the at least one reproductive cell indicator includes at least one indicator of a property of the reproductive cell; a property of administering the at least one energy supplying factor to the reproductive cell; a property of the modified reproductive cell; a property of administering at least one additional round of an energy supplying factor to a modified reproductive cell; reproductive cell or tissue apoptosis; reproductive cell division; reproductive cell cytoskeletal rearrangement; reproductive cell mitochondrial quality, quantity, or arrangement; reproductive cell fertilization success or failure; or reproductive cell or tissue secretion.

In an embodiment, a method of modifying a reproductive cell includes selecting at least one reproductive cell for modifying by injecting the at least one exogenous energy supplying factor. In an embodiment, the at least one reproductive cell is selected for modifying based on one or more reproductive cell parameters. In an embodiment, the one or more reproductive cell parameters include at least one of reproductive cell size, reproductive cell stage, reproductive cell quality, health of the subject from which the reproductive cell originates, species of the subject from which the reproductive cell originates, or storage conditions of the reproductive cell. In an embodiment, the storage conditions of the reproductive cell include at least one of duration of storage time, storage temperature, storage size, reproductive cell dilution, or storage solution(s). In an embodiment, the reproductive cell includes at least one of a germ cell, gametogonium, or gamete. In an embodiment, the reproductive cell includes at least one of an oogonium, primary oocyte, secondary oocyte, ootid, ovum, polar body, follicular cell, cumulus cell, spermatogonia, primary spermatocyte, secondary spermatocyte, spermatid, spermatozoa, Sertoli cell, or Leydig cell.

In an embodiment, a method of modifying at least one reproductive cell includes selecting at least one reproductive cell for manipulation. In an embodiment, manipulation includes utilizing the selected reproductive cell for at least one fertilization event. In an embodiment, manipulation includes at least one of cell membrane stripping, genetic modification, freezing, fusing with another reproductive cell, or fusing with a somatic cell. In an embodiment, selecting the at least one reproductive cell for manipulation is based at least in part on at least one of detected exogenous energy supplying factor, or detected endogenous energy supplying factor. In an embodiment, selecting the at least one reproductive cell for manipulation is based at least in part on at least one of the size of the reproductive cell, cleavage rate of the reproductive cell, metabolic profile of the reproductive cell, genomic profile of the reproductive cell, transcriptomic profile of the reproductive cell, or proteomic profile of the reproductive cell.

In an embodiment, a method of restoring mitochondrial function in a reproductive cell includes administering to a subject containing at least one reproductive cell, an amount and for a time sufficient to increase endogenous ATP levels of at least one of the subject's reproductive cells, of at least one of an angiotensin receptor blocker or an angiotensin converting enzyme inhibitor. In an embodiment, the angiotensin receptor inhibitor includes angiotensin-II receptor blocker (ARB).

In an embodiment, a method of modifying a reproductive cell includes providing at least one of creatine, phosphorcreatine, or creatine kinase to a reproductive cell. In an embodiment, the reproductive cell is located in a subject.

In an embodiment, a method for up-regulating mitochondrial function in a reproductive cell includes actively introducing at least one exogenous energy supplying factor into at least one intracellular compartment of a reproductive cell.

In an embodiment, a method of modifying an oocyte includes introducing at least one exogenous energy supplying factor into at least one intracellular compartment of an oocyte. In an embodiment, introducing includes allowing at least one exogenous energy supply factor to diffuse into the at least one intracellular compartment of the oocyte. In an embodiment, introducing at least one exogenous energy supplying factor includes liposomal introduction by way of endocytosis.

In an embodiment, a method of modifying a female reproductive cell includes introducing at least one exogenous energy supplying factor into at least one intracellular compartment of a female reproductive cell. In an embodiment, the female reproductive cell includes at least one of an oogonium, primary oocyte, secondary oocyte, ootid, ovum, polar body, follicular cell, or cumulus cell.

In an embodiment, a method of modifying a reproductive cell includes introducing at least one exogenous constituent into at least one intracellular compartment of a reproductive cell, the exogenous constituent configured to increase at least one endogenous energy supplying factor.

In an embodiment, a method of selecting at least one reproductive cell includes detecting at least one endogenous energy supplying factor in at least one reproductive cell, and scoring the at least one reproductive cell based on the detection. In an embodiment, detecting includes measuring the amount of at least endogenous energy supplying factor in at least one reproductive cell, and scoring the at least one reproductive cell based on the measurement. In an embodiment, the method of modifying at least one reproductive cell includes selecting at least one reproductive cell based on the score.

In an embodiment, the method of modifying at least one reproductive cell includes manipulating the at least one reproductive cell selected. In an embodiment, manipulating the at least one reproductive cell includes utilizing the at least one reproductive cell in a fertilization event. In an embodiment, manipulating the at least one reproductive cell includes freezing the at least one reproductive cell. In an embodiment, manipulating the at least one reproductive cell includes genetically modifying the at least one reproductive cell. In an embodiment, manipulating the at least one reproductive cell includes supplying additional exogenous energy supplying factors, or other agents to the at least one reproductive cell. In an embodiment, manipulating the at least one reproductive cell includes stripping the cell membrane of the at least one reproductive cell.

In an embodiment, a modified reproductive cell is produced by the process of introducing at least one exogenous energy supplying factor into at least one intracellular compartment of the reproductive cell. In an embodiment, the introducing includes actively or passively introducing the at least one exogenous energy supplying factor. In an embodiment, the reproductive cell has not yet completed meiosis. In an embodiment, the reproductive cell has not yet entered meiosis. In an embodiment, the reproductive cell has not yet completed mitosis. In an embodiment, the reproductive cell has not yet entered mitosis. In an embodiment, the reproductive cell has not yet completed phase I of meiosis.

In an embodiment, the reproductive cell is implantable or transplantable. In an embodiment, the reproductive cell is implanted or transplanted into at least one subject. In an embodiment, the reproductive cell is implanted or transplanted into at least one subject subsequent to modification. In an embodiment, the reproductive cell is implanted subsequent to modification, into the original subject from which it was extracted.

In an embodiment, the reproductive cell includes, but is not limited to, at least one of a germ cell, gametegonium, gamete, or reproductive supporting cell. In an embodiment, the reproductive cell includes but is not limited to at least one oogonium, primary oocyte, secondary oocyte, ootid, ovum, polar body, follicular cell, granulosa cell, cumulus cell, spermatogonia, primary spermatocyte, secondary spermatocyte, spermatid, spermatozoa, Sertoli cell, or Leydig cell.

In an embodiment, an increase in intracellular ATP-level is sufficient to remedy the impairment of oocyte mitotic spindle, or impairment of sperm cell motility. In an embodiment, the energy supplying factor (e.g., ATP) is provided to a germ cell, gamete, or supporting cell in order to enhance intracellular energy levels (e.g., ATP levels), or compensate for energy level deficiency (e.g., ATP deficiency). In an embodiment, ATP serves as the energy supplying factor, and is provided to a developing gamete, such as an oocyte, prior to or during oocyte meosis phase I.

In an embodiment, the energy supplying factor (e.g., creatine) is supplied by either general administration or specific, localized administration. In an embodiment, the energy supplying factor (e.g., creatine) is supplied by at least one of peroral delivery, oral delivery, topical delivery, transdermal delivery, epidermal delivery, intravitreal delivery, transmucosal delivery, inhalation, surgical delivery, or injection delivery.

In an embodiment, a modified reproductive cell includes at least one exogenous energy supplying factor. In an embodiment, the exogenous energy supplying factor is delivered to the cytoplasm of the modified reproductive cell. In an embodiment, the exogenous energy supplying factor is delivered to at least one mitochondrion of the modified reproductive cell.

In an embodiment, the at least one exogenous energy supplying factor includes at least one of exogenous creatine, exogenous phosphocreatine, exogenous creatine kinase, exogenous chlorophyll, exogenous lactate, exogenous glucose or other carbohydrate, exogenous calcium or other mineral, exogenous ATP, exogenous ADP, exogenous AMP, or a precursor thereof.

In an embodiment, at least one reproductive cell is selected for modification based on one or more reproductive cell parameters. In an embodiment, the one or more reproductive cell parameters relate to at least one property of the reproductive cell. In an embodiment, the one or more reproductive cell parameters include at least one of reproductive cell size, reproductive cell stage, reproductive cell quality, health of the subject from which the reproductive cell originates, species of the subject from which the reproductive cell originates, cleavage rate of the reproductive cell, metabolic profile of the reproductive cell, genomic profile of the reproductive cell, transcriptomic profile of the reproductive cell, proteomic profile of the reproductive cell, or storage conditions of the reproductive cell (if previously stored ex vivo). In an embodiment, the storage conditions of the reproductive cell include at least one of duration of storage time, storage temperature, storage size, reproductive cell dilution, or storage solution(s).

In an embodiment, the at least one subject includes at least one of a plant, alga, or animal. In an embodiment, the at least one subject includes at least one of a vertebrate or invertebrate. In an embodiment, the at least one subject includes at least one of an amphibian, mammal, reptile, fish, or bird. In an embodiment, the at least one subject includes at least one human. In an embodiment, the at least one plant includes at least one of a food crop, ornamental, aquatic plant. In an embodiment, the at least one plant includes at least one flowering plant, herb, shrub, bush, tree, or vegetable.

In an embodiment, a method includes detecting at least one reproductive cell indicator. In an embodiment, the at least one reproductive cell indicator includes at least one of a property of the reproductive cell (such as a reproductive cell parameter as discussed herein); a property of administering the at least one energy supplying factor to the reproductive cell; a property of the modified reproductive cell; a property of administering at least one additional round of an energy supplying factor to a modified reproductive cell; reproductive cell or tissue apoptosis; reproductive cell division; reproductive cell cytoskeletal rearrangement; reproductive cell mitochondrial quality, quantity, or arrangement; reproductive cell fertilization success or failure; or reproductive cell or tissue secretion.

In an embodiment, the detection material includes at least one of a radioactive, luminescent, colorimetric fluorescent, or odorous substance. In an embodiment, the at least one detection material includes at least one of a taggant, contrast agent, sensor, or electronic identification device. In an embodiment, the at least one electronic identification device includes at least one radio frequency identification device. In an embodiment, the at least one sensor receives information associated with at least one of temperature, pH, inflammation, presence of at least one substance, or biological response to administration of the composition. In an embodiment, the at least one detection material includes at least one of a diamagnetic particle, ferromagnetic particle, paramagnetic particle, super paramagnetic particle, particle with altered isotope, or other magnetic particle.

In an embodiment, a method of modifying a reproductive cell includes delivering at least one exogenous energy supplying factor to the intracellular compartment of a reproductive cell. In an embodiment, the energy supplying factor (e.g., ATP) is injected, infused, diffused, electroporated, or otherwise delivered to the intracellular compartment of a reproductive cell.

In an embodiment, the method further includes detecting at least one endogenous energy supplying factor in the reproductive cell prior to delivering the at least one exogenous energy supplying factor thereto. In an embodiment, the method further includes measuring at least one endogenous energy supplying factor in the reproductive cell prior to delivering the at least one exogenous energy supplying factor thereto. In an embodiment, the at least one exogenous energy supplying factor is delivered in response to the presence or level of at least one endogenous energy supplying factor in the reproductive cell, thus regulating the overall level of the energy supplying factor in the reproductive cell.

In an embodiment, the method further includes detecting or measuring the level of the at least one exogenous energy supplying factor in the reproductive cell subsequent to delivery thereto. In an embodiment, the at least one exogenous energy supplying factor is provided in response to the presence or level of at least one exogenous energy supplying factor in the reproductive cell. In an embodiment, the at least one exogenous energy supplying factor is provided in response to the presence or level of at least one reproductive cell indicator, as described herein.

In an embodiment, delivering at least one exogenous energy supplying factor includes injecting the reproductive cell with at least one exogenous energy supplying factor, for example, by intracytoplasmic injection. In an embodiment, delivering at least one exogenous energy supplying factor to the intracellular compartment of a reproductive cell includes providing the at least one exogenous energy supplying factor to the intracellular mitochondria of the reproductive cell.

Oocyte microinjection, including intracytoplasmic sperm injection (ICSI) involves precise maneuver of the oocyte for injection of an agent (e.g., in the case of ICSI, the oocyte is injected directly with a single live sperm cell for fertilization). As discussed herein, particularly in the Examples section, the procedure includes a female animal subject who has undergone ovarian stimulation with fertility medications that result in maturation of one or more oocytes. The oocytes are aspirated, for example by utilizing vaginal ultrasound for guidance, and incubated. The semen sample is typically prepared by centrifuging in medium in order to separate live sperm cells from debris and most of the dead sperm cells. A single live sperm cell is then isolated from the resultant live sperm fraction, and is injected into the oocyte.

Moreover, electroporation is reportedly used for successful gene transfer into spermatozoa cells of various species of fish. See, e.g., Tsai, *Mol. Rep. and Dev.* vol. 56, pp. 281-284 (2000), which is incorporated herein by reference.

In an embodiment, a method of maintaining or restoring mitochondrial function in a reproductive cell, or reproductive cell vigor, includes administering to a subject containing at least one reproductive cell, a sufficient amount of at least one exogenous energy supplying factor, or at least one agent that promotes endogenous production or retention of at least one endogenous energy supplying factor. Likewise, in an embodiment, a method of maintaining or restoring reproductive cell vigor in a subject includes administering to the subject containing at least one reproductive cell, a sufficient amount of at least one exogenous energy supplying factor, or at least one agent that promotes endogenous production or retention of at least one endogenous energy supplying factor. In an embodiment, mitochondrial function is assessed, for example, by measuring the mitochondrial membrane potential ($\Delta\psi_m$). Methods to measure mitochondrial membrane potential are known in the art, and are described in detail herein at the Examples section.

Administering angiotensin receptor inhibitor or angiotensin converting enzyme inhibitor to human subjects reportedly results in an increase in blood creatine levels. See, e.g., Palmer, *Nephrol. Dial. Transplant.* Vol. 18, pp. 1973-1975 (2003), which is incorporated herein by reference.

In an embodiment, a method of maintaining or restoring reproductive cell vigor includes administering to a subject containing at least one reproductive cell, an angiotensin receptor blocker (ARB) or an angiotensin converting enzyme inhibitor (ACE-I) sufficient to increase the endogenous ATP level of at least one of the reproductive cells. In an embodiment, the angiotensin receptor blocker includes angiotensin-II receptor blocker.

In an embodiment, the intracellular levels of ATP are increased in a subject by way of providing creatine supplementation to the subject. For example, creatine monohydrate has been reported to provide benefits when consumed by human adults. See, e.g., Brose, et al., *J. Gerontaol. A. Biol. Sci. Med. Sci.*, vol. 58, no. 1, pp. 11-9 (2003), which is incorporated herein by reference. In an embodiment, creatine supplementation is administered to a subject containing at least one reproductive cell, in a sufficient amount to increase the intracellular level of ATP in at least one reproductive cell of the subject.

In an embodiment, for example, creatine monohydrate is provided to a human subject as at least 1 gram/day, at least 2 grams/day, at least 3 grams/day, at least 4 grams/day, at least 5 grams/day, at least 6 grams/day, at least 7 grams/day, at least 8 grams/day, at least 9 grams/day, at least 10 grams/day, at least 11 grams/day, at least 12 grams/day, at least 13 grams/day, at least 14 grams/day, at least 15 grams/day, at least 16 grams/day, at least 17 grams/day, at least 18 grams/day, at least 19 grams/day, at least 20 grams/day, at least 21 grams/day, at least 22 grams/day, at least 23 grams/day, at least 24 grams/day, at least 25 grams/day, at least 26 grams/day, at least 27 grams/day, at least 28 grams/day, at least 29 grams/day, at least 30 grams/day, at least 31 grams/day, at least 32 grams/day, at least 33 grams/day, at least 34 grams/day, at least 35 grams/day, at least 36 grams/day, at least 37 grams/day, at least 38 grams/day, at least 39 grams/day, at least 40 grams/day, or any value less than or therebetween, for a duration of approximately 1 day, approximately 2 days, approximately 3 days, approximately 4 days, approximately 5 days, approximately 6 days, approximately 7 days, approximately 8 days, approximately 9 days, approximately 10 days, approximately 11 days, approximately 12 days, approximately 13 days, approximately 14 days, approximately 3 weeks, approximately 4 weeks, approximately 5 weeks, approximately 6 weeks, approximately 7 weeks, approximately 8 weeks, approximately 9 weeks, approximately 10 weeks, approximately 11 weeks, approximately 12 weeks, approximately 13 weeks, approximately 14 weeks, approximately 15 weeks, approximately 16 weeks, approximately 17 weeks, approximately 18 weeks, approximately 19 weeks, approximately 20 weeks, or any value therebetween. In an embodiment, the creatine supplementation continues until a successful pregnancy develops. In an embodiment, the creation supplementation continues until a successful harvest of at least one reproductive cell is completed.

Creatine supplementation can be provided to the subject by any standard method, including oral delivery, peroral delivery, injection, topical delivery, transdermal delivery, epidermal delivery, intravitreal delivery, transmucosal delivery, inhalation, or surgical delivery. The creatine supplementation is formulated according to the route of administration.

In an embodiment, an implantable delivery device comprises: a housing including at least one reservoir containing a composition including at least one exogenous energy supplying factor; the reservoir configured to receive, retain, and dispense at least a portion of the composition to at least one reproductive cell or tissue; and at least one component configured to administer the composition to the at least one reproductive cell or tissue.

Kits

In an embodiment, kits are included for any of the various aspects disclosed herein. For example, in an embodiment, a kit includes a detection material responsive to at least one reproductive cell indicator, and means for administering at least one exogenous energy supplying factor to at least one reproductive cell. In an embodiment, the kit includes the at least one exogenous energy supplying factor. In an embodiment, the kit includes a delivery device. In an embodiment, the kit includes at least one tool for selecting at least one reproductive cell for manipulation. In an embodiment, a kit includes standard packaging or instructions for use.

As indicated in the Figures, FIG. 1 illustrates 100 a delivery device, comprising: 110 a housing including at least one reservoir containing at least one composition including at least one exogenous energy supplying factor; the reservoir configured to receive, retain, and dispense at least a portion of the composition to at least one reproductive cell or tissue. In an embodiment, 115, the delivery device is implantable. In an embodiment, 120, wherein the at least one composition further includes at least one pharmaceutically-acceptable carrier or excipient.

In an embodiment 130, the housing includes one or more ports. In an embodiment 140, at least one of the one or more ports includes at least one outlet port or at least one inlet port. In an embodiment 150, the device further comprises one or more controllable output mechanisms operably linked to the one or more ports to control dispensing of at least a portion of the composition from the at least one reservoir. In an embodiment 155, the at least one controllable output mechanism includes at least one of a micropump, valve, or actuator. In an embodiment 160, the valve includes at least one of a one-way valve, or pressure settable valve. In an embodiment 170, the actuator includes at least one of a piezoelectric actuator, electrostatic actuator, thermal actuator, shape-memory alloy actuator, bioactuator, or magnetic actuator. In an embodiment 175, the at least one controllable output mechanism includes at least one thermal or nonthermal gate in communication with the at least one outlet port of the at least one reservoir.

As illustrated in FIG. 2, in an embodiment 200, the device further comprises at least one control circuitry configured to control the at least one controllable output mechanism. In an embodiment 205, the at least one control circuitry is configured to generate and transmit an electromagnetic control signal. In an embodiment 210, the device further comprises at least one memory mechanism for storing instructions for generating and transmitting the electromagnetic control signal. In an embodiment 220, the at least one control circuitry is configured for time-release of at least a portion of the at least one composition from the at least one reservoir.

In an embodiment 230, the at least one control circuitry is configured for variable programming control of the at least one controllable output mechanism. In an embodiment 240, the at least one control circuitry is configured to control the release of the composition. In an embodiment 250, the at least one control circuitry is configured to control at least one of the rate of release, amount of release, or time of release of the composition. In an embodiment 260, the at least one control circuitry is configured to generate and transmit an electromagnetic control signal configured to control the at least one controllable output mechanism. In an embodiment 270, the at least one control circuitry is configured to control the at least one controllable output mechanism for time-release of at least a portion of the composition from the at least one reservoir. In an embodiment 280, the at least one control circuitry is configured for variable programming control of the at least one controllable output mechanism.

In an embodiment 290, the at least one control circuitry is configured to control release of the composition or a portion thereof in response to a signal from a sensor. In an embodiment 300, the signal represents information from at least one reproductive cell indicator. In an embodiment 310, the at least one or more reproductive cell indicator includes at least one of a property of the reproductive cell, a property of administering the at least one energy supplying factor to the reproductive cell; a property of the modified reproductive cell; a property of administering at least one additional round of an energy supplying factor to a modified reproductive cell; reproductive cell or tissue apoptosis; reproductive cell division; reproductive cell cytoskeletal rearrangement; reproductive cell mitochondrial quality, quantity, or arrangement; reproductive cell fertilization success or failure; or reproductive cell or tissue secretion.

Figure 3:
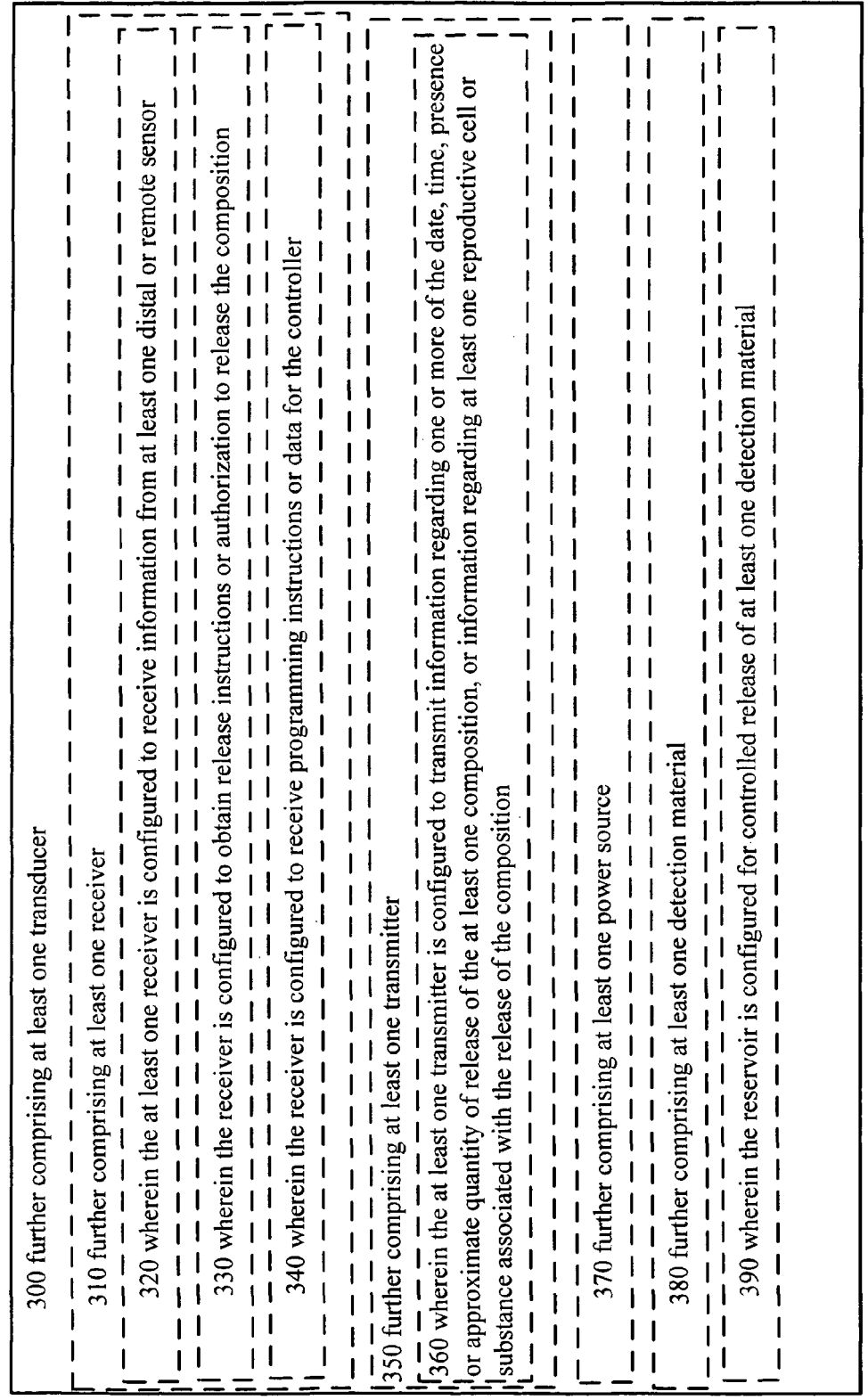
FIG. 3 illustrates a partial view of various embodiments of the device of FIG. 1.

As illustrated in FIG. 3, in an embodiment, the device further comprises at least one transducer. In an embodiment 310, the device further comprises at least one receiver. In an embodiment 320, the at least one receiver is configured to receive information from at least one distal or remote sensor. In an embodiment 330, the receiver is configured to obtain release instructions or authorization to release the composition. In an embodiment 340, the receiver is configured to receive programming instructions or data for the controller.

In an embodiment 350, the device further comprises at least one transmitter. In an embodiment 360, the at least one transmitter is configured to transmit information regarding one or more of the date, time, presence or approximate quantity of release of the at least one composition, or information regarding at least one reproductive cell or substance associated with the release of the composition.

In an embodiment 370, the device further comprises at least one power source. In an embodiment 380, the device further comprises at least one detection material. In an embodiment 390, the reservoir is configured for controlled release of at least one detection material.

As illustrated in FIG. 4, in an embodiment 400, the at least one detection material includes at least one of a radioactive, luminescent, colorimetric, fluorescent, or odorous substance. In an embodiment 410, the at least one detection material includes at least one of a taggant, contrast agent, or electronic identification device. In an embodiment 420, the at least one electronic identification device includes at least one radio frequency identification device. In an embodiment 430, the delivery device further comprises at least one sensor. In an embodiment 440, the at least one sensor is configured to receive information associated with at least one of temperature, pH, inflammation, presence of at least one substance, detection material, or biological response to administration of the composition. In an embodiment 450, the delivery device further comprises a controller configured to respond to the at least one sensor. In an embodiment 460, the at least one detection material includes at least one of a diamagnetic particle, ferromagnetic particle, paramagnetic particle, super paramagnetic particle, particle with altered isotope, or other magnetic particle. In an embodiment 470, the at least one detection material is responsive to at least one of the presence or level of the composition; or the presence or level of at least one reproductive cell or substance associated with the dispensing of the composition. In an embodiment 480, the at least one detection material is responsive to the approximate quantity of at least one of the composition, or at least one reproductive cell or substance associated with the release of the composition.

As illustrated in FIG. 5, the at least one detection material is responsive to at least one of: enzyme, acid, amino acid, peptide, polypeptide, protein, oligonucleotide, nucleic acid, ribonucleic acid, oligosaccharide, polysaccharide, glycopeptide, glycolipid, lipoprotein, sphingolipid, glycosphingolipid, glycoprotein, peptidoglycan, lipid, carbohydrate, metalloprotein, proteoglycan, chromosome, adhesion molecule, cytokine, chemokine, immunoglobulin, antibody, antigen, platelet, extracellular matrix, blood plasma, cell wall, hormone, organic compound, inorganic compound, salt, or cell ligand. In an embodiment 510, the at least one detection material is responsive to at least one of: glucose, lactate, urea, uric acid, glycogen, oxygen, carbon dioxide, carbon monoxide, ketone, nitric oxide, nitrous oxide, alcohol, alkaloid, pH, albumin, ATP, NADH, $FADH_2$, pyruvate, creatinine, cholesterol, alpha-fetoprotein, chorionic gonadotropin, estrogen, progesterone, testosterone, thyroxine, melatonin, calcitonin, antimullerian hormone, angiotensin, follicle-stimulating hormone, gonadotropin-releasing hormone, mitochondria, growth hormone, growth hormone-releasing hormone, insulin, human placental lactogen, oxytocin, luteinizing hormone, prolactin, cortisol, aldosterone, estradiol, estriol, estrone, leukotriene, vitamin, mineral, renin, DHEA, DHT, alloisoleucine, or a precursor of any thereof.

In an embodiment 520, the device further comprises at least one memory mechanism for storing instructions for generating and transmitting an electromagnetic control signal. In an embodiment 530, the device further comprises at least one imaging apparatus capable of imaging the approximate quantity within a treatment region relating to at least one of the composition; at least one reproductive cell, or at least one substance associated with dispensing the composition. In an embodiment 540, the device further comprises at least one memory location for recording information related to sensing information, imaging information, transmitting information, or other information related to the delivery device. In an embodiment 550, the at least one memory location is configured to record information regarding at least one sensor. In an embodiment 560, the at least one memory location is configured to record information regarding at least one of a sensed condition, history, or performance of the device.

As illustrated in FIG. 6, in an embodiment 600, the at least one memory location is configured to record information regarding one or more of the date, time, presence or approximate quantity of at least one of the administered composition; or at least one reproductive cell or substance associated with the dispensing of the composition. In an embodiment 610, the at least one reproductive cell or substance associated with dispensing of the composition includes at least one of an organic or inorganic small molecule, nucleic acid, amino acid, peptide, polypeptide, protein, glycopeptide, glycoprotein, glycolipid, lipopolysaccharide, peptidoglycan, proteoglycan, lipid, lipoprotein, glycospingolipid, metalloprotein, liposome, chromosome, nucleus, acid, base, buffer, protic solvent, aprotic solvent, carbohydrate, ATP, creatine, lactate, phosphocreatine, pyruvate, glucose, lipopolysaccharide, vitamin, mineral, cytokine, chemokine, antibody, element, hormone, virus, enzyme, oligonucleotide, ribonucleic acid, oligosaccharide, polysaccharide, adhesion molecule, NADH, $FADH_2$, estrogen, progesterone, testosterone, thyroxine, corticotrophin-releasing hormone, follicle-stimulating hormone, gonadotropin-releasing hormone, growth hormone, growth hormone-releasing hormone, insulin, oxytocin, luteinizing hormone, leptin, prolactin, cortisol, aldosterone, estradiol, estriol, estrone, DHEA, DHT, germ cell, gametegonium, gamete, or reproductive supporting cell. In an embodiment, the reproductive cell includes but is not limited to at least one oogonium, primary oocyte, secondary oocyte, ootid, ovum, polar body, follicular cell, granulosa cell, cumulus cell, spermatogonia, primary spermatocyte, secondary spermatocyte, spermatid, spermatozoa, Sertoli cell, or Leydig cell.

In an embodiment 620, the device further comprises at least one information transmission mechanism configured to transmit information recorded by the at least one electronic memory location. In an embodiment 630, the device is located in or is substantially in the form of one or more of a spray apparatus, pump apparatus, bioreactor, or drilling apparatus. In an embodiment 640, the device is substantially in the form of one or more of a patch, oral inhaler, nasal spray or other orifice spray, iontophoretic apparatus, oral consumable, ocular or otic dropper or spray, stent, shunt, orifice insert, ductal implant, organ implant, orifice spray or inhaler, sutures, surgical staples, bandages, micro-electromechanical device, nano-electromechanical device, or absorbable mesh. In an embodiment 650, the device further comprises one or more inlet mechanisms for receiving external delivery of the at least one composition.

Figure 7:
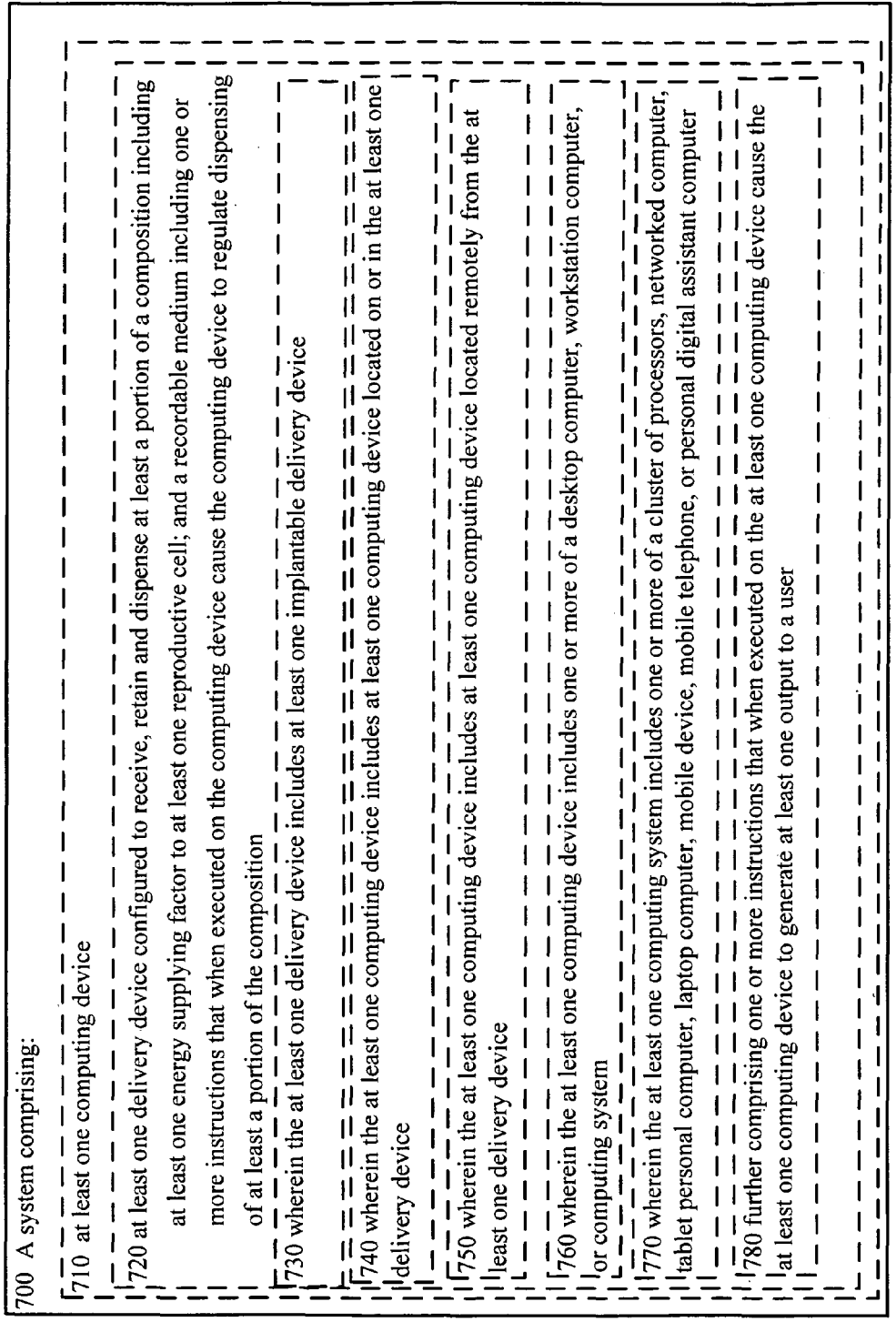
FIG. 7 illustrates a partial view of a particular embodiment of a system disclosed herein.

As illustrated in FIG. 7, in an embodiment 700, a system comprises: 710 at last one computing device, 720 at least one delivery device configured to receive, retain and dispense at least a portion of a composition including at least one energy supplying factor to at least one reproductive cell; and a recordable medium including one or more instructions that when executed on the computing device cause the computing device to regulate dispensing of at least a portion of the composition. In an embodiment 730, the at least one delivery device includes at least one implantable delivery device. In an embodiment 740, wherein the at least one computing device includes at least one computing device located on or in the at least one delivery device. In an embodiment 750, the at least one computing device includes at least one computing device located remotely from the at least one delivery device. In an embodiment 760, the at least one computing device includes one or more of a desktop computer, workstation computer, or computing system. In an embodiment 770, the at least one computing system includes one or more of a cluster of processors, networked computer, tablet personal computer, laptop computer, mobile device, mobile telephone, or personal digital assistant computer. In an embodiment 780, the system further comprises one or more instructions that when executed on the at least one computing device cause the at least one computing device to generate at least one output to a user.

Figure 8:
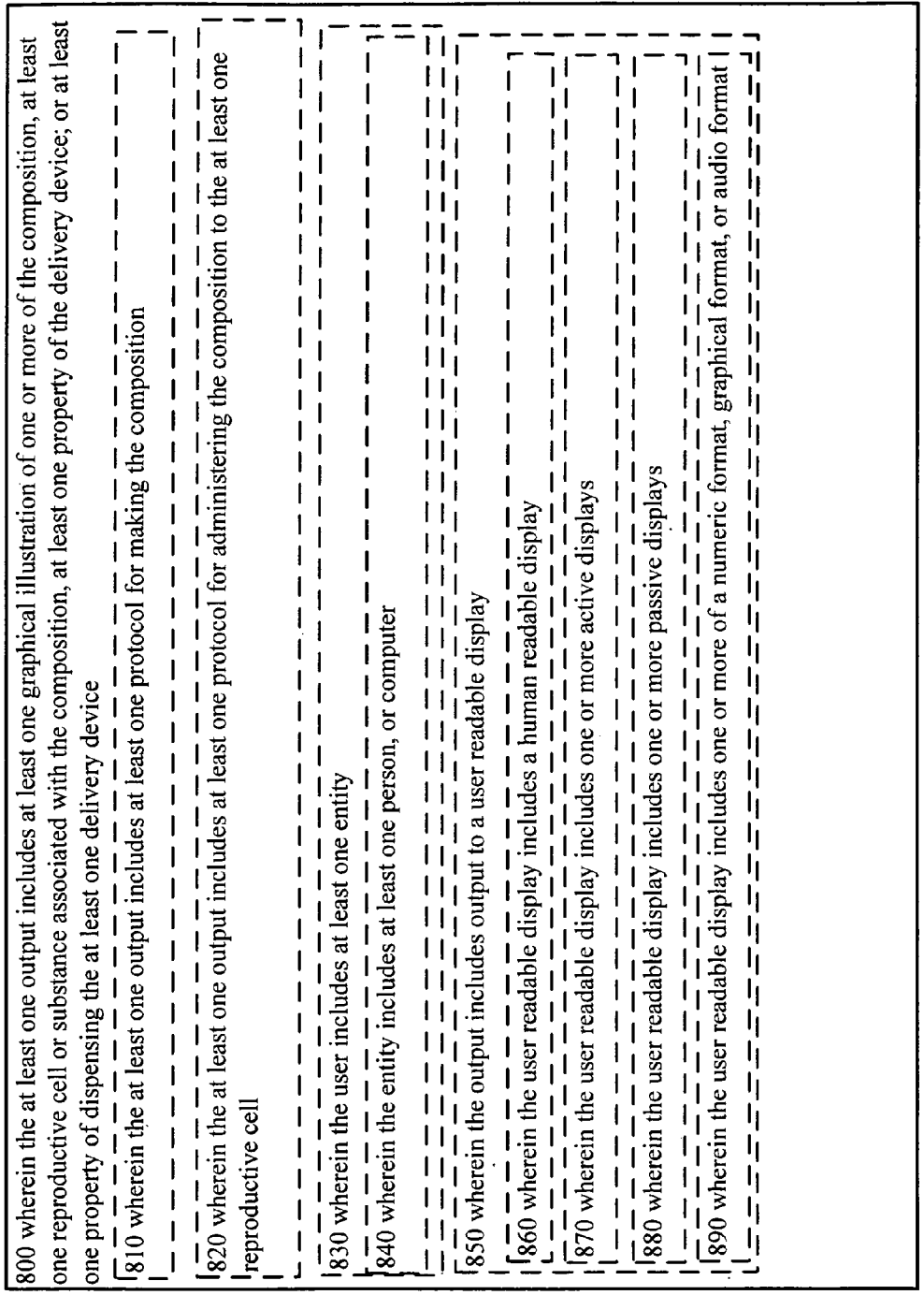
FIG. 8 illustrates a partial view of various embodiments of the system of FIG. 7.

As illustrated in FIG. 8, in an embodiment 800, the at least one output includes at least one graphical illustration of one or more of the composition, at least one reproductive cell or substance associated with the composition, at least one property of the delivery device; or at least one property of dispensing the at least one delivery device. In an embodiment 810, the at least one output includes at least one protocol for making the composition. In an embodiment 820, the at least one output includes at least one protocol for administering the composition to the at least one reproductive cell. In an embodiment 830, the user includes at least one entity. In an embodiment 840, the entity includes at least one person, or computer. In an embodiment 850, the output includes output to a user readable display. In an embodiment 860, the user readable display includes a human readable display. In an embodiment 870, the user readable display includes one or more active displays. In an embodiment 880, the user readable display includes one or more passive displays. In an embodiment 890, the user readable display includes one or more of a numeric format, graphical format, or audio format.

As illustrated in FIG. 9, the system further comprises one or more instructions for determining one or more parameters for selecting the at least one reproductive cell from other reproductive cells. In an embodiment 910, the system further comprises one or more instructions for determining one or more parameters for administering the composition to at least one reproductive cell. In an embodiment 920, the system further comprises one or more instructions for receiving information related to one or more reproductive cell indicators prior to, during, or subsequent to administering the composition to the at least one reproductive cell. In an embodiment 930, the information related to one or more reproductive cell indicators includes information from at least one of an assay, image, or gross assessment of the at least one reproductive cell or reproductive cell related tissue prior to, during, or subsequent to administering the composition. In an embodiment 940, the assay includes at least one technique including spectroscopy, microscopy, electrochemical detection, polynucleotide detection, histological examination, biopsy analysis, fluorescence resonance energy transfer, electron transfer, enzyme assay, electrical conductivity, isoelectric focusing, chromatography, immunoprecipitation, immunoseparation, aptamer binding, filtration, electrophoresis, immunoassay, or radioactive assay.

In an embodiment 950, the at least one image includes one or more images acquired by at least one of laser, holography, x-ray crystallography, optical coherence tomography, computer-assisted tomography scan, computed tomography, magnetic resonance imaging, positron-emission tomography scan, ultrasound, x-ray, electrical-impedance monitoring, microscopy, spectrometry, flow cytommetry, radioisotope imaging, thermal imaging, infrared visualization, multiphoton calcium-imaging, photography, or in silico generation.

Figure 10:
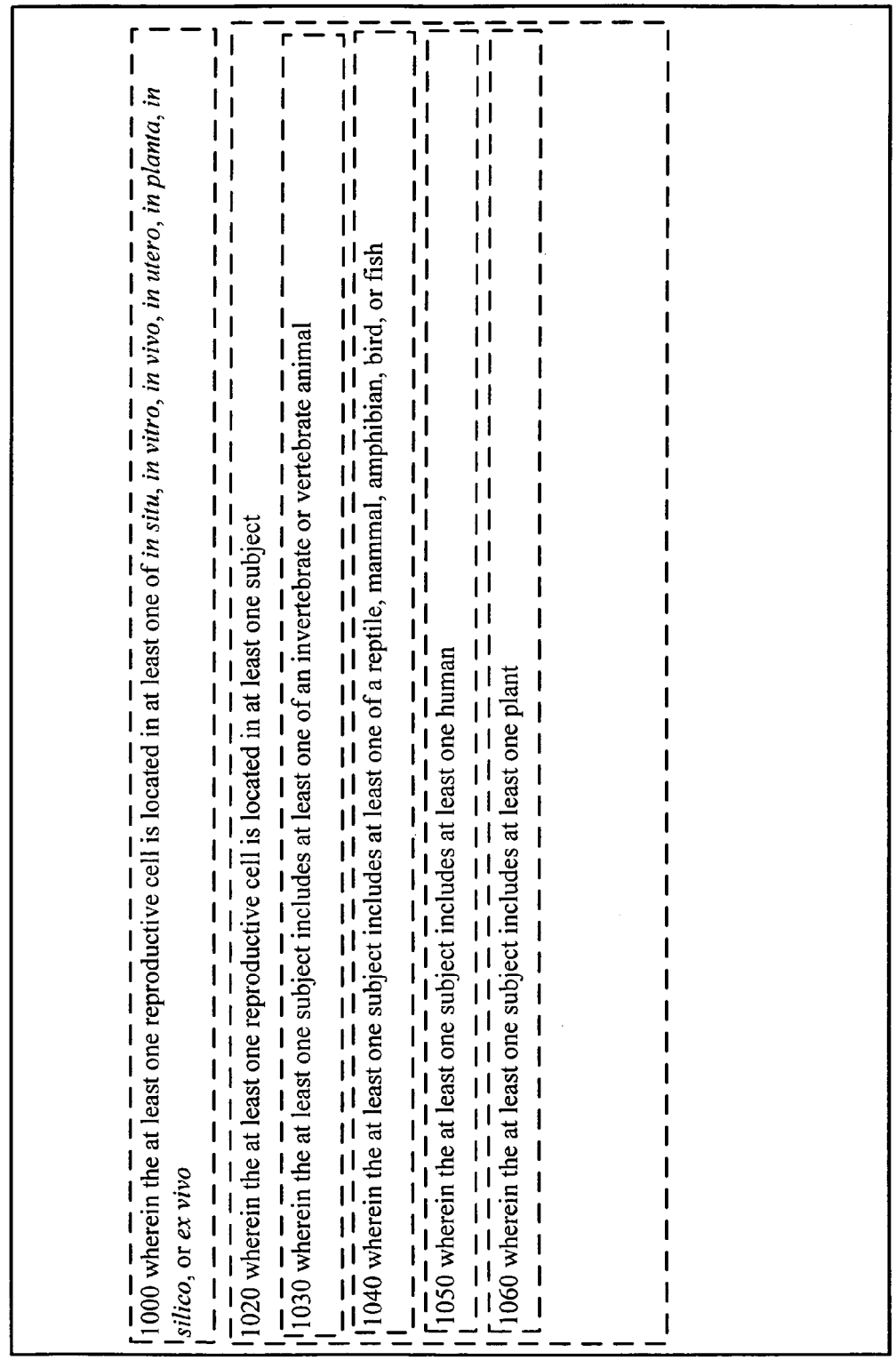
FIG. 10 illustrates a partial view of various embodiments of the system of FIG. 7.

As illustrated in FIG. 10, in an embodiment 1000, the at least one reproductive cell is located in at least one of in situ, in vitro, in vivo, in utero, in planta, in silico, or ex vivo. In an embodiment 1020, the at least one reproductive cell is located in at least one subject. In an embodiment 1030, the at least one subject includes at least one of an invertebrate or vertebrate animal. In an embodiment 1040, the at least one subject includes at least one of a reptile, mammal, amphibian, bird, or fish. In an embodiment 1050, the at least one subject includes at least one human. In an embodiment 1060, the at least one subject includes at least one plant.

As illustrated in FIG. 11, in an embodiment 1100, a computer program product comprises: 1110 a recordable medium bearing one or more instructions for regulating dispensing of at least one delivery device to at least one reproductive cell, wherein the delivery device includes a composition including at least one exogenous energy supplying factor, and generating at least one output. In an embodiment 1120, the recordable medium includes a computer-readable medium. In an embodiment 1130, the recordable medium includes a communications medium. In an embodiment 1140, the computer program product further comprises one or more instructions for receiving information related to one or more reproductive cell indicators prior to, during, or subsequent to administering the composition. In an embodiment 1160, the output includes at least one protocol for making the composition. In an embodiment 1170, the output includes at least one protocol for administering the composition to at least one reproductive cell. In an embodiment 1180, the output includes at least one graphical illustration of one or more of the composition, or at least one reproductive cell or substance associated with the at least one reproductive cell, at least one property of the at least one delivery device, or at least one property of dispensing the at least one delivery device. In an embodiment 1190, the computer program product further comprises one or more instructions for displaying results of the processing.

As illustrated in FIG. 12, in an embodiment 1200, a computer-implemented method comprises: 1210 regulating dispensing a composition from at least one delivery device to at least one reproductive cell, the composition including at least one energy supplying factor. In an embodiment 1220, the at least one delivery device includes at least one implantable delivery device. In an embodiment 1230, the computer-implemented method further comprises generating at least one output. In an embodiment 1240, the generating at least one output includes generating at least one output to a user. In an embodiment 1250, the user includes at least one entity. In an embodiment 1260, the entity includes at least one person, or computer. In an embodiment 1270, the at least one output includes at least one graphical illustration of one or more of the composition, or at least one reproductive cell or substance associated with the at least one reproductive cell; at least one property of the at least one delivery device; or at least one property of dispensing the at least one delivery device. In an embodiment 1280, the at least one output includes at least one protocol for making the composition based on one or more parameters of the at least one reproductive cell. In an embodiment 1285, the at least one output includes one or more parameters for selecting the at least one reproductive cell from other reproductive cells.

As illustrated in FIG. 13, in an embodiment 1300, the at least one output includes at least one protocol for dispensing the at least one composition to the at least one reproductive cell. In an embodiment 1302, the dispensing the at least one composition to the at least one reproductive cell includes dispensing the at least one composition in response to one or more reproductive cell indicators. In an embodiment 1305, the at least one output includes at least one output to a user readable display. In an embodiment 1308, the user readable display includes a human readable display. In an embodiment 1310, the user readable display includes one or more active displays. In an embodiment 1320, the user readable display includes one or more passive displays. In an embodiment 1330, the user readable display includes one or more of a numeric format, graphical format, or audio format. In an embodiment 1340, the computer-implemented method further comprises receiving information related to one or more reproductive cell indicators prior to, during, or subsequent to administering the composition to the at least one reproductive cell. In an embodiment 1350, the receiving information related to one or more reproductive cell indicators includes information from at least one of an assay, image, or gross assessment of the at least one biological tissue prior to, during, or subsequent to administering the composition.

As illustrated in FIG. 14, in an embodiment 1400, the assay includes at least one technique including spectroscopy, microscopy, electrochemical detection, polynucleotide detection, histological examination, biopsy analysis, fluorescence resonance energy transfer, electron transfer, enzyme assay, electrical conductivity, isoelectric focusing, chromatography, immunoprecipitation, immunoseparation, aptamer binding, filtration, electrophoresis, immunoassay, or radioactive assay. In an embodiment 1420, the at least one image includes one or more images acquired by at least one of laser, holography, x-ray crystallography, optical coherence tomography, computer-assisted tomography scan, computed tomography, magnetic resonance imaging, positron-emission tomography scan, ultrasound, x-ray, electrical-impedance monitoring, microscopy, spectrometry, flow cytommetry, radioisotope imaging, thermal imaging, infrared visualization, multiphoton calcium-imaging, photography, or in silico generation. In an embodiment 1440, the at least one reproductive cell is located in at least one of in situ, in vitro, in vivo, in utero, in planta, in silico, or ex vivo. In an embodiment 1450, the at least one reproductive cell is at least partially located in at least one subject. In an embodiment 1460, the at least one subject includes at least one of an invertebrate or vertebrate animal. In an embodiment 1470, the at least one subject includes at least one of a reptile, mammal, amphibian, bird, or fish. In an embodiment 1480, the at least one subject includes at least one human. In an embodiment 1490, the at least one subject includes at least one plant.

PROPHETIC EXAMPLES

Example 1

Method to Provide ATP to Oocytes from a Female Subject of Advanced Age Undergoing in vitro Fertilization A female subject who is at an advanced maternal age, 43 years old, undergoes ovarian stimulation to induce maturation of multiple follicles and produce oocytes, which are harvested by transvaginal oocyte retrieval. The harvested oocytes are tested with a mitochondrial membrane potential assay to assess their overall health. Based on the assay results, ATP encapsulated in liposomes is delivered to the cytoplasm of the harvested oocytes in need thereof. The modified oocytes are reanalyzed to assess oocyte quality prior to selection for in vitro fertilization (IVF) and cryopreservation.

Methods to stimulate multiple ovarian follicles and isolate multiple oocytes are known in the art (see e.g., Rossato et al., *Hum. Reprod.* 14: 694-697, 1999 which is incorporated herein by reference). Ovarian stimulation is accomplished by administering a gonadotrophin releasing hormone analog (e.g., triptorelin, Trelstar La available from Watson Pharma, Inc., Corona, Calif.), and follicle stimufating hormone (FSH; e.g., Follistim® AQ available from Schering Plough, Kenilworth, N.J.). FSH treatments are given for approximately 9 days and the follicles are monitored by vaginal ultrasound until the follicles reach a diameter greater than about 18 mm. Then human chorionic gonadotrophin (HCG, 10,000 IU; e.g., Pregnyl®, available from Schering Plough, Kenilworth, N.J.) is administered. Approximately 36 hours after HCG administration the oocytes are retrieved by transvaginal aspiration. Procedures and devices for transvaginal ultrasonography and aspiration of ovarian follicles are known in the art (see e.g., Wang and Sauer, *Therap. and Clinical Risk Mgmt,* 2: 355-364, 2006 which is incorporated herein by reference). The retrieved oocytes are tested to assess mitochondrial health.

Individual oocytes are tested for their oxygen respiration rate using a real-time, noninvasive system (see e.g., Scott et al., *Rep. Biomed. Online* 17: 461-469, 2008, which is incorporated herein by reference). Oocytes are classified microscopically as immature (germinal vesicle and metaphase I oocytes) or metaphase II oocytes. Oocytes are washed free of all cannulus and granulosa cells and placed in individual wells of a glass tray in Sage Complete Embryo Culture medium (available from Sage In vitro Fertilization, Inc., Trumbull, Conn.). Oxygen respiration rate measurements are made with microelectrodes that measure the steady-state diffusive oxygen flux toward oocytes placed in the bottom of narrow wells in culture trays. An instrument for measuring respiration rates in oocytes, EmbryoScope™, is available from Unisense Fertilitech, Aarhus, Denmark. A baseline respiration rate (BRR) is calculated from repeated measurement of the oxygen concentration gradients in the well over an initial 5 hour time period. The mean BRR for oocytes from mothers greater than 40 years old is significantly lower ($P<0.01$) than that for mothers less than 35 years of age (BRR=0.461 nL $O_2$/hr versus BRR=0.575 nL $O_2$/hr respectively (see e.g., Scott et al., Ibid.) In addition, all oocytes are tested to determine their mitochondrial membrane potentials.

Mitochondrial membrane potential ($\Delta\psi$) is a key indicator of mitochondrial health and metabolic activity. Methods to measure $\Delta\psi$ in live cells are known in the art (see e.g., Distelmaier et al., *Cytometry Part A*, 73A: 129-138, 2008, which is incorporated herein by reference). To measure $\Delta\psi_m$, oocytes are incubated with a fluorescent cationic dye, tetramethyl rhodamine methyl ester (TMRM; available from Life Technologies Corp., Carlsbad, Calif.), that is taken up and sequestered by mitochondria. Oocytes are incubated in Medium 199 (available from Life Technologies Corp., Carlsbad, Calif.) containing 100 nM TMRM for about 25 minutes at 37° C., and then washed with phosphate buffered saline (PBS). To measure TMRM fluorescence, an inverted microscope (available from Carl Zeiss Microimaging, Inc., Thornwood, N.Y.) with an X63 oil immersion objective is used and the oocytes are maintained at 37° C. in a heated chamber. TMRM sequestered within mitochondria is excited with 540 nm wavelength light for approximately 100 milliseconds, and fluorescent images emitted at approximately 565 nm are captured on a CoolSNAP HQ monochrome CCD-camera (available from Roper Scientific Photometrics, Vianen, The Netherlands). Image processing and analysis are performed using Image Pro Plus 5.1 software (available from Media Cybernetics, Silver Spring, Md.) and Origin Pro 7.5 software (available from Originlabs, Northampton, Mass.). Small changes in $\Delta\psi_m$ (e.g., approximately 12 millivolts) are seen as a reduction in average fluorescence intensity from the mitochondria in an oocyte. A mean $\Delta\psi_m$ of approximately $-119$ millivolts is seen for healthy normal cells. See, e.g., Distelmaier et al., Ibid.)

Oocytes with diminished $\Delta\psi_m$ are cultured with ATP encapsulated in liposomes to supplement cytoplasmic ATP. Oocytes are cultured in media comprised of follicular fluid (obtained during follicle aspiration) and a balanced salt solution, e.g., Ham's F10 media. Liposomes containing 36-38 mole percent of ATP ((moles of ATP/moles of lipid)×100) are added to the cultures to deliver approximately 2 pmole of ATP to the cytoplasm of each oocyte to promote oocyte health (see e.g., Van Blerkom et al., *Hum. Reprod.* 10: 415-424, 1995 which is incorporated herein by reference). Methods to prepare liposomes containing ATP are known in the art (see e.g., Liang et al., *J. Microencapsulation*, 21: 251-261, 2004; and U.S. Pat. No. 7,056,529; each of which is incorporated herein by reference).

Liposomes comprised of phosphatidyl choline and cholesterol are combined with a 400 mM ATP solution and subjected to a freeze thaw process, and then purified (see e.g., Liang et al., Ibid.; lipids and ATP are available from Sigma-Aldrich, St. Louis, Mo.). Alternatively liposomes loaded with ATP are commercially available from FormuMax Scientific Inc., Palo Alto, Calif. Oocytes are cultured at about 37° C. with ATP-loaded liposomes in approximately 5% $CO_2$ and 95% air for about 4-8 hours (see e.g., U.S. Pat. No. 5,563,059, which is incorporated herein by reference). Oocyte quality is assessed by measuring $\Delta\psi$, and by microscopic inspection (see e.g., Van Blerkom et al., Ibid.) which is incorporated herein by reference).

Normal appearing oocytes with a normal distribution of cytoplasmic organelles and a $\Delta\psi_m$ of $-119$ millivolts are selected for IVF and cryopreservation. Selected oocytes are fertilized in vitro with approximately 100,000 spermatozoa per oocyte. Methods to collect and prepare spermatozoa and to inseminate oocytes are known in the art (see e.g., Rossato et al., Ibid.). Fertilization is evaluated microscopically after 16-20 hours by identification of pronuclei, and 46-48 hours after insemination the embryos are classified by the number and shape of blastomeres and the percentage of fragments. Alternatively, healthy oocytes with a $\Delta\psi_m$ of approximately $-119$ millivolts are frozen for future use. Germinal vesicle, metaphase I and metaphase II oocytes are frozen using a slow freezing method (see e.g., Tao and Del Valle, *J. Assist. Reprod. Genet.* 25: 287-296, 2008 which is incorporated herein by reference). Oocytes are treated with a cryoprotectant (e.g., dimethyl sulfoxide available from Sigma-Aldrich, St. Louis, Mo.) and step-wise cooled to $-7°$ C. at $-1°$ C./min; then cooled to $-35°$ C. at $-0.3°$ C./min; then cooled rapidly to $-80°$ C. and ultimately plunged into liquid nitrogen (at $-196°$ C.). Each oocyte is stored under liquid nitrogen in a microculture dish with its individual well location referenced to a computer address. Information stored on the computer includes: the oocyte's microscopic evaluation, respiration rate, $\Delta\psi_m$, and the mother's identity, medical history, and genetic information.

Example 2

Implanted Device to Supply ATP by Microinjection to Oocytes Within Ovarian Follicles and Improve the Quality of Oocytes that are Selected for in vitro Fertilization A female subject of advanced maternal age, 40 years of age, is treated with fertility drugs to stimulate follicle development in her ovaries. Follicle development is stimulated by administering a gonadotrophin releasing hormone analog (e.g., triptorelin, Trelstar La available from Watson Pharma, Inc., Corona, Calif.) and follicle stimulating hormone (FSH; e.g., Follistim® AQ available from Schering Plough, Kenilworth, N.J.). FSH treatments are given for approximately 9 days and the follicles are monitored by vaginal ultrasound until the follicles reach a diameter of approximately 12 mm.

Guided by ultrasound imaging each follicle of approximately 12 mm in diameter is implanted with a micro-electromechanical system (MEMS) device. The MEMS device contains a sensor for an oocyte indicator, a reservoir, a nanopump to deliver liposomal ATP, and a Radio Frequency Identification (RFID) tag. The MEMS sensor detects oxygen in follicular fluid, an indicator of oocyte health, and delivers liposomes containing ATP to oocytes in follicles with low oxygen levels (see e.g., U.S. Patent Application No. 2008/0091119, which is incorporated herein by reference).

The oocyte indicator is monitored twice daily by the MEMS device and additional doses of liposomal ATP are delivered as required. The MEMS device contains a RFID tag that identifies the follicle and links data on oxygen levels and liposomal ATP delivered to a specific follicle. A RFID reader and remote computing device store and evaluate the cumulative data for each follicle and its associated oocyte.

Micro-electromechanical system devices are injected into ovarian follicles to sense an indicator of oocyte health, and to deliver liposomal ATP. A MEMS device is constructed with an oxygen sensor to assess the $O_2$ content of follicular fluid. For example, an implanted microsensor that detects oxygen levels in the range of 0-50 mm Hg and transmits data to an external receiver is known in the art (see e.g., U.S. Pat. No. 7,010,340, which is incorporated herein by reference). A wireless, implantable MEMS device (see e.g., Product Sheet from Integrated Sensing Systems, Ypsilanti, Mich., which is incorporated herein by reference) is transvaginally injected into each follicle guided by ultrasound imaging, and the oxygen concentration in individual follicles is transmitted wirelessly to a computing device. The oxygen concentration for each follicle is measured twice daily, and the data are stored and analyzed on a computing device. Circuitry on the MEMS device detects electronic signals from the oxygen sensor corresponding to suboptimal oxygen concentrations (e.g., less than 50 mm Hg) and actuates a nanopump to deliver liposomal ATP contained in a reservoir on the MEMS device. The nanopump delivers a liposomal ATP suspension at a flow rate of approximately 50 milliliters/(min.cm$^2$) to the follicular fluid and the oocyte. (See e.g., U.S. Pat. No. 7,540,717, which is incorporated herein by reference). Liposomes containing 36-38 mole percent of ATP ((moles of ATP/moles of lipid)×100) are administered to deliver approximately 2 pmole of ATP to the cytoplasm of the oocyte. Methods to prepare liposomes containing ATP are known in the art (see e.g., Liang et al., *J. Microencap.*, 21: 251-261, 2004; and U.S. Pat. No. 7,056,529, each of which are incorporated herein by reference). Liposomes comprised of phosphatidyl choline and cholesterol are combined with a 400 mM ATP solution and subjected to a freeze thaw process and then purified (see e.g., Liang et al., Ibid.; lipids and ATP are available from Sigma-Aldrich, St. Louis, Mo.). Alternatively, liposomes loaded with ATP are commercially available from FormuMax Scientific Inc., Palo Alto, Calif.

Follicular development is monitored using vaginal ultrasonography and oocytes are retrieved by aspiration of the follicles. When follicles are approximately 18 mm in diameter human chorionic gonadotrophin (HCG, 10,000 IU; e.g., Pregnyl®, available from Schering Plough, Kenilworth, N.J.) is administered and approximately 36 hours after HCG administration the oocytes are retrieved by transvaginal aspiration. Procedures and devices for transvaginal ultrasonography and aspiration of ovarian follicles are known in the art (see e.g., Wang and Sauer, *Therap. and Clin. Risk Mgmt.*, 2: 355-364, 2006, which is incorporated herein by reference). Follicular fluid containing an oocyte and the MEM device with a micro-RFID tag (see e.g., Product Sheet from Hitachi Europe, Ltd., Maidenhead, Berkshire, U.K., which is incorporated herein by reference) is cultured in vitro prior to in vitro fertilization of the oocyte. For example, an RFID tag, such as the Hitatchi Mu-chip, is a passive tag that requires no battery, and is manufactured to enable the chip to operate in heat and moisture (Product Sheet Hitachi RFID Solutions, Ibid.) A RFID reader (available from Hitachi Europe, Ltd., Maidenhead, Berkshire, U.K.) is used to detect the MEMS device. The RFID reader is also used to link the follicle with the corresponding oocyte and the accumulated data on oxygen levels, as well as the amount of liposomal ATP delivered. Moreover, the RFID tag is used to identify the female subject who produced the oocyte as well as the associated data on her medical history, genetics, and the dose and schedule of her fertility drugs.

Retrieved oocytes are tested in vitro in order to select the healthiest oocytes for in vitro fertilization and cryopreservation. As mentioned, the mitochondrial membrane potential ($\Delta\psi_m$) is a key indicator of mitochondrial health and metabolic activity. Methods to measure $\Delta\psi$ in live cells are known in the art (see e.g., Distelmaier et al., *Cytometry Part A*, 73A: 129-138, 2008, which is incorporated herein by reference). To measure $\Delta\psi_m$, oocytes are incubated with a fluorescent cationic dye, tetramethyl rhodamine methyl ester (TMRM; available from Life Technologies Corp., Carlsbad, Calif.), that is taken up and sequestered by mitochondria. Oocytes are incubated in Medium 199 (available from Life Technologies Corp., Carlsbad, Calif.) containing 100 nM TMRM for about 25 minutes at 37° C., and then washed with phosphate buffered saline (PBS). In order to measure TMRM fluorescence, an inverted microscope (available from Carl Zeiss Microimaging, Inc., Thornwood, N.Y.) with an X63 oil immersion objective is used, and the oocytes are maintained at 37° C. in a heated chamber. TMRM sequestered within mitochondria is excited with 540 nm wavelength light for approximately 100 milliseconds and fluorescent images emitted at approximately 565 nm are captured on a CoolSNAP HQ monochrome CCD-camera (available from Roper Scientific Photometrics, Vianen, The Netherlands). Image processing and analysis are performed using Image Pro Plus 5.1 software (available from Media Cybernetics, Silver Spring, Md.) and Origin Pro 7.5 software (available from Originlabs, Northampton, Mass.). Small changes in $\Delta\psi_m$ (e.g., approximately 12 millivolts) are seen as a reduction in average fluorescence intensity from the mitochondria in an oocyte. A mean $\Delta\psi_m$ of approximately −119 millivolts is seen for healthy normal cells (see e.g., Distelmaier et al., Ibid). Oocytes with a mean $\Delta\psi_m$ of approximately −119 millivolts and a heterogeneous distribution of mitochondria clustered around the nuclear membrane (characteristic of oocytes in metaphase I or II) are selected for in vitro fertilization and cryopreservation (see e.g., Wang et al., *J. of Zhejiang Univ. Sci. B* 10: 483-492 (2009) which is incorporated herein by reference).

Selected oocytes are fertilized in vitro with approximately 100,000 spermatozoa per oocyte. Methods to collect and prepare spermatozoa and to inseminate oocytes are known in the art (see e.g., Rossato et al., Ibid.). Fertilization is evaluated microscopically after 16-20 hours by identification of pronuclei, and 46-48 hours after insemination the embryos are classified for the number and shape of blastomeres and the percentage of fragments. Alternatively, healthy oocytes with a $\Delta\psi_m$ of approximately −119 millivolts are frozen for future use. Germinal vesicle, metaphase I oocytes, and metaphase II oocytes are frozen using a slow freezing method (see e.g., Tao and Del Valle, *J. Assist. Reprod. Genet.* 25: 287-296, 2008, which is incorporated herein by reference). Oocytes are treated with a cryoprotectant (e.g., dimethyl sulfoxide available from Sigma-Aldrich, St. Louis, Mo.) and then cooled to −7° C. at a rate of −1° C./min; then cooled to −35° C. at −0.3° C./min; then cooled rapidly to −80° C. and ultimately plunged into liquid nitrogen (at −196° C.). Each oocyte is stored under liquid nitrogen in a microculture dish with its MEMS device and RFID tag identifying the oocyte and linking it to information stored on a computer that includes: the oocyte's

Example 3

A Method to Provide Phosphocreatine to Oocytes in vitro to Improve the Quality and Quantity of Oocytes Suitable for in vitro Fertilization and Cryopreservation A female subject who is at an advanced maternal age undergoes ovarian stimulation to induce multiple follicles and oocytes which are harvested by ultrasound-guided transvaginal oocyte retrieval. The oocytes are tested with a mitochondrial membrane potential ($\Delta\psi_m$) assay to assess their health. Based on the assay results, phosphocreatine is delivered to the cytoplasm of the oocytes as needed. Following in vitro maturation, the modified oocytes are reanalyzed to assess oocyte quality prior to selection for in vitro fertilization (IVF) and cryopreservation.

Methods to stimulate multiple ovarian follicles and isolate multiple oocytes are known in the art (see e.g., Rossato et al., Hum. Reprod. 14: 694-697, 1999 which is incorporated herein by reference). Ovarian stimulation is accomplished by administering a gonadotrophin releasing hormone analog (e.g., triptorelin, Trelstar La available from Watson Pharma, Inc., Corona, Calif.) and follicle stimulating hormone (FSH; e.g., Follistim® AQ available from Schering Plough, Kenilworth, N.J.). FSH treatments are given for approximately 9 days and the follicles are monitored by vaginal ultrasound until the follicles reach a diameter greater than about 18 mm.

Next, human chorionic gonadotrophin (HCG, 10,000 IU; e.g., Pregnyl®, available from Schering Plough, Kenilworth, N.J.) is administered and approximately 36 hours after HCG administration, the oocytes are retrieved by transvaginal aspiration. Procedures and devices for transvaginal ultrasonography and aspiration of ovarian follicles are known in the art (see e.g., Wang and Sauer, Therap. and Clin. Risk Mgt., 2: 355-364 (2006), which is incorporated herein by reference). The retrieved oocytes are tested to assess mitochondrial health.

The mitochondrial membrane potential ($\Delta\psi_m$) is a key indicator of mitochondrial health and metabolic activity. Methods to measure $\Delta\psi_m$ in live cells are known in the art (see e.g., Distelmaier et al., Cytometry Part A, 73A: 129-138 (2008), which is incorporated herein by reference). To measure $\Delta\psi_m$, oocytes are incubated with a fluorescent cationic dye, tetramethyl rhodamine methyl ester (TMRM; available from Life Technologies Corp., Carlsbad, Calif.), that is taken up and sequestered by mitochondria. Oocytes are incubated in Medium 199 (available from Life Technologies Corp., Carlsbad, Calif.) containing 100 nM TMRM for about 25 minutes at 37° C., and then washed with phosphate buffered saline (PBS). To measure TMRM fluorescence, an inverted microscope (available from Carl Zeiss Microimaging, Inc., Thornwood, N.Y.) with an X63 oil immersion objective is used, and the oocytes are maintained at 37° C. in a heated chamber. TMRM sequestered within mitochondria is excited with 540 nm wavelength light for approximately 100 milliseconds, and fluorescent images emitted at approximately 565 nm are captured on a CoolSNAP HQ monochrome CCD-camera (available from Roper Scientific Photometrics, Vianen, The Netherlands). Image processing and analysis are performed using Image Pro Plus 5.1 software (available from Media Cybernetics, Silver Spring, Md.) and Origin Pro 7.5 software (available from Originlabs, Northampton, Mass.). Small changes in $\Delta\psi_m$ (e.g., approximately 12 millivolts) are seen as a reduction in average fluorescence intensity from the mitochondria in an oocyte. A mean $\Delta\psi_m$ of approximately −119 millivolts is seen in healthy, normal cells. See, e.g., Distelmaier et al., Ibid.

Oocytes with diminished $\Delta\psi_m$ are microinjected with phosphocreatine to supplement cytoplasmic energy stores. Methods to microinject mammalian oocytes are know in the art (see e.g., U.S. Patent Application No. 2003/0157086, which is incorporated herein by reference). For microinjection, six picoliters of 330 millimolar phosphocreatine (available from Sigma-Aldrich, St. Louis, Mo.) is microinjected into single oocytes using a Zeiss Axiovert 135 inverted microscope equipped with Narishige micromanipulators and a PL-100 pico-injector (microscope, micromanipulators and injector are available from Tritech Research, Los Angeles, Calif.). Oocytes are cultured in media comprised of follicular fluid (obtained during follicle aspiration) and a balanced salt solution, e.g., Ham's F10 media. Oocytes are cultured at about 37° C. in approximately 5% $CO_2$ and 95% air for about 4-8 hours (see e.g., U.S. Pat. No. 5,563,059, which is incorporated herein by reference). Oocyte quality is assessed by measuring $\Delta\psi$, and by microscopic inspection (See e.g., Van Blerkom et al., Human Rep. 10: 415-424, 1995 which is incorporated herein by reference). Normal appearing oocytes with a normal distribution of cytoplasmic organelles and a $\Delta\psi_m$ of about −119 millivolts are selected for in vitro fertilization, and cryopreservation.

Oocyte quality is assessed by measuring $\Delta\psi_m$ and by microscopic inspection (See e.g., Van Blerkom et al., Human Rep. 10: 415-424 (1995), which is incorporated herein by reference). Normal appearing oocytes with a normal distribution of cytoplasmic organelles, and a $\Delta\psi_m$ of −119 millivolts are selected for in vitro fertilization and cryopreservation.

Selected oocytes are fertilized in vitro with approximately 100,000 spermatozoa per oocyte. Methods to collect and prepare spermatozoa and to inseminate oocytes are known in the art (see e.g., Rossato et al., Ibid.). Fertilization is evaluated microscopically after 16-20 hours by identification of pronuclei, and 46-48 hours after insemination the embryos are classified based on the number and shape of blastomeres, as well as the percentage of fragments. Alternatively, healthy oocytes with a $\Delta\psi_m$ of approximately −119 millivolts are frozen for future use. Germinal vesicle, metaphase I oocytes, and metaphase II oocytes are frozen using a slow freezing method (see e.g., Tao and Del Valle, J. Assist. Reprod. Genet. 25: 287-296, 2008, which is incorporated herein by reference). Oocytes are treated with a cryoprotectant (e.g., dimethyl sulfoxide, available from Sigma-Aldrich, St. Louis, Mo.), and then cooled to −7° C. at a rate of −1° C./min; then cooled to −35° C. at −0.3° C./min; then cooled rapidly to −80° C. and ultimately plunged into liquid nitrogen (at −196° C.). Each oocyte is stored under liquid nitrogen in a microculture dish with its individual well location referenced to a computer address. Information stored on the computer includes: the oocyte's microscopic evaluation, $\Delta\psi_m$, the female subject's identity, medical history, and genetic information.

Example 4

Implanted Devices to Supply Lipid Encapsulated ATP to Oocytes in vivo to Improve the Quality and Quantity of Oocytes Retrieved for in vitro Fertilization or Cryopreservation A female subject of advanced maternal age, 40 years of age, is treated with hormones to stimulate follicle development in her ovaries. Methods to stimulate multiple ovarian follicles and isolate multiple oocytes are known in the art (see e.g., Rossato et al., *Hum. Reprod.* 14: 694-697 (1999), which is incorporated herein by reference). Follicle development is stimulated by administering a gonadotrophin releasing hormone analog (e.g., triptorelin, Trelstar La available from Watson Pharma, Inc., Corona, Calif.), and follicle stimulating hormone (FSH; e.g., Follistim® AQ available from Schering Plough, Kenilworth, N.J.). FSH treatments are given for approximately 9 days and the follicles are monitored by vaginal ultrasound until antral follicles are apparent. Guided by vaginal ultrasound imaging, each antral follicle is injected with a micro-electromechanical system (MEMS) device using a dedicated syringe (available from Irvine Scientific, Santa Ana, Calif.). The MEMS device contains a sensor for an oocyte indicator, a reservoir, a nanopump to deliver liposomal ATP, and a RFID tag. The MEMS sensor detects NADH levels in follicular fluid, an indicator of oocyte health which correlates with levels of intracellular ATP (see e.g., Nadlinger et al., *Biochim. et Biophys. Acta* 1573: 177-182 (2003), which is incorporated herein by reference). Circuitry on the MEMS device detects diminished levels of follicular NADH, and signals delivery of liposomes containing ATP to the oocyte. The oocyte indicator is monitored twice daily by the MEMS device and additional doses of liposomal ATP are delivered as required. The MEMS device contains a RFID tag that identifies the follicle, and also links data on oxygen levels and liposomal ATP delivered to a specific follicle. A RFID reader and remote computing device store and evaluate the cumulative data for each follicle and its associated oocyte.

Micro-electromechanical system devices are injected into ovarian follicles to sense an indicator of oocyte health and to deliver liposomal ATP. A MEMS device is constructed with a NADH sensor to assess the NADH concentration in follicular fluid. For example, an implanted microsensor that detects biological chemicals and transmits data to an external receiver is known in the art (see e.g., U.S. Pat. No. 7,010,340, which is incorporated herein by reference). Moreover sensors for in vivo detection of NADH based on fluorimetry are described (see e.g., Mayevsky and Rogatsky, *Am. J. Phys.* 292: 615-640 (2007), which is incorporated herein by reference). A wireless, implantable MEMS device (see e.g., Product Sheet from Integrated Sensing Systems, Ypsilanti, Mich. which is incorporated herein by reference) is transvaginally injected into each follicle guided by ultrasound imaging, and the NADH concentration in individual follicles is transmitted wirelessly to a computing device. The NADH concentration for each follicle is measured twice daily, and the data are stored and analyzed on a computing device. Circuitry on the MEMS device detects electronic signals from the NADH sensor corresponding to changes in NADH concentration, and actuates a nanopump to deliver liposomal ATP contained in a reservoir on the MEMS device. The nanopump delivers a liposomal ATP suspension at a flow rate of approximately 50 milliliters/(min.cm$^2$) to the follicular fluid and the oocyte (see e.g., U.S. Pat. No. 7,540,717, which is incorporated herein by reference).

Liposomes containing 36-38 mole percent of ATP ((moles of ATP/moles of lipid)×100) are administered to deliver approximately 2 pmole of ATP to the cytoplasm of the oocyte. Methods to prepare liposomes containing ATP are known in the art (see e.g., Liang et al., *J. Microencap.,* 21: 251-261 (2004); and U.S. Pat. No. 7,056,529, each of which are incorporated herein by reference). Liposomes comprised of phosphatidyl choline and cholesterol are combined with 400 mM ATP solution and subjected to a freeze thaw process, and subsequently purified (see e.g., Liang et al., Ibid.; lipids and ATP are available from Sigma-Aldrich, St. Louis, Mo.). Alternatively, liposomes loaded with ATP are commercially available from FormuMax Scientific Inc., Palo Alto, Calif.

Follicular development is monitored using vaginal ultrasonography and oocytes are retrieved by aspiration of the follicles. When follicles are approximately 18 mm in diameter human chorionic gonadotrophin (HCG, 10,000 IU; e.g., Pregnyl®, available from Schering Plough, Kenilworth, N.J.) is administered, and approximately 36 hours after HCG administration the oocytes are retrieved by transvaginal aspiration. Procedures and devices for transvaginal ultrasonography and aspiration of ovarian follicles are known in the art (see e.g., Wang and Sauer, *Therap. and Clin. Risk Mgt,* 2: 355-364 (2006), which is incorporated herein by reference). Follicular fluid containing an oocyte and the MEMS device with a micro RFID tag (see e.g., Product Sheet from Hitachi Europe, Ltd., Maidenhead, Berkshire, U.K., which is incorporated herein by reference) is cultured in vitro prior to in vitro fertilization of the oocyte. A RFID reader (available from Hitachi Europe, Ltd., Maidenhead, Berkshire, U.K.) is used to detect the MEMS device, as well as link the follicle and the corresponding oocyte with the accumulated data on NADH levels and the amount of liposomal ATP delivered. Moreover the RFID tag identifies the female subject who produced the oocyte as well as the associated data on her medical history, genetics, and the dose and schedule of her fertility drugs.

Individual oocytes are tested for their oxygen respiration rate using a real-time, noninvasive system (see e.g., Scott et al., *Rep. Biomed.* Online 17: 461-469 (2008), which is incorporated herein by reference). Oocytes are classified microscopically as immature (germinal vesicle and metaphase I oocytes), or metaphase II oocytes. Oocytes are washed free of all cannulus and granulosa cells, and placed in individual wells of a glass tray in Sage Complete Embryo Culture medium (available from Sage In vitro Fertilization, Inc., Trumbull, Conn.). Oxygen respiration rate measurements are made with microelectrodes that measure the steady-state diffusive oxygen flux toward oocytes placed in the bottom of narrow wells in culture trays. An instrument for measuring respiration in oocytes is commercially available, for example, EmbryoScope™, Unisense Fertilitech, Aarhus, Denmark. A baseline respiration rate (BRR) is calculated from repeated measurement of the oxygen concentration gradients in the well over an initial 5 hour time period. The mean BRR for oocytes from female subjects greater than 40 years old is significantly lower ($P<0.01$) than that for female subjects less than 35 years of age (BRR=0.461 nL $O_2$/hr versus BRR=0.575 nL $O_2$/hr respectively; see e.g., Scott et al., Ibid.) In addition, all oocytes are tested to determine their mitochondrial membrane potentials.

Mitochondrial membrane potential ($\Delta\psi_m$) is a key indicator of mitochondrial health and metabolic activity. Methods to measure $\Delta\psi_m$ in live cells are known in the art (see e.g., Distelmaier et al., *Cytometry Part A,* 73A: 129-138 (2008), which is incorporated herein by reference). To measure $\Delta\psi_m$, oocytes are incubated with a fluorescent cationic dye, tetramethyl rhodamine methyl ester (TMRM; available from Life Technologies Corp., Carlsbad, Calif.), that is taken up and sequestered by mitochondria. Oocytes are incubated in Medium 199 (available from Life Technologies Corp., Carlsbad, Calif.) containing 100 nM TMRM for about 25 minutes at 37° C., and then washed with phosphate buffered saline (PBS). To measure TMRM fluorescence, an inverted microscope (available from Carl Zeiss Microimaging, Inc., Thornwood, N.Y.) with an X63 oil immersion objective is used, and the oocytes are maintained at 37° C. in a heated chamber.

TMRM sequestered within mitochondria is excited with 540 nm wavelength light for approximately 100 milliseconds, and fluorescent images emitted at approximately 565 nm are captured on a CoolSNAP HQ monochrome CCD-camera (available from Roper Scientific Photometrics, Vianen, The Netherlands). Image processing and analysis are performed using Image Pro Plus 5.1 software (available from Media Cybernetics, Silver Spring, Md.) and Origin Pro 7.5 software (available from Originlabs, Northampton, Mass.). Small changes in $\Delta\psi_m$ (e.g., approximately 12 millivolts) are seen as a reduction in average fluorescence intensity from the mitochondria in an oocyte. A mean $\Delta\psi_m$ of approximately −119 millivolts is seen for healthy, normal cells. See, e.g., Distelmaier et al., Ibid.)

Oocytes are selected for fertilization and cryopreservation based on their NADH levels, respiration rate and $\Delta\psi_m$. Selected oocytes are fertilized in vitro with approximately 100,000 spermatozoa per oocyte. Methods to collect and prepare spermatozoa and to inseminate oocytes are known in the art (see e.g., Rossato et al., Ibid.). Fertilization is evaluated microscopically after 16-20 hours by identification of pronuclei, and 46-48 hours after insemination, the embryos are classified for the number and shape of blastomeres and the percentage of fragments. Alternatively, healthy oocytes with a $\Delta\psi_m$ of approximately −119 millivolts and a BRR equal to approximately 0.575 nL $O_2$/hr are frozen for future use. Metaphase I oocytes and metaphase II oocytes are frozen using a slow freezing method (see e.g., Tao and Del Valle, *J. Assist. Reprod. Genet.* 25: 287-296 (2008), which is incorporated herein by reference). Oocytes are treated with a cryoprotectant (e.g., dimethylsulfoxide available from Sigma-Aldrich, St. Louis, Mo.) and then cooled in a step-wise fashion, first to −7° C. at a rate of −1° C./min; then cooled to −35° C. at −0.3° C./min; then cooled rapidly to −80° C., and ultimately plunged into liquid nitrogen (at −196° C.). Each oocyte is stored under liquid nitrogen in a microculture dish with its MEMS device, and RFID tag for identifying the oocyte and linking it to information stored on a computer. The information includes: the oocyte's microscopic evaluation, NADH levels, liposomal ATP delivered, respiration rate, $\Delta\psi_m$ and the female subject's identity, medical history, and genetic information.

Example 5

A Method to Provide ATP to a Plant Embryo that Promotes Growth and Development of the Plant Embryo A horticulturist injects maize (*Zea mays*) embryos with ATP to promote the development of a high percentage of plant embryos that survive and grow vigorously. Native plant embryos derive from pollination of ovules and fusion of sperm and egg cells to form a zygote. The zygotic embryo develops into a mature embryo or seed that stores food and energy supplies for use during germination and seedling growth.

In order to increase the level of the energy substrate, ATP in fertilized maize embryos they are isolated, microinjected with ATP, cultured in vitro and planted. Fertilized embryos of maize are isolated from Zea mays plants grown to maturity. Methods to isolate plant embryos are known in the art (see e.g., U.S. Pat. No. 6,300,543, which is incorporated herein by reference). Maize plants with silks 6-10 cm in length are pollinated by hand and the plants are placed in a growth chamber for at least 16 hours to allow fertilization to occur. Ovaries are isolated by removing husks and silks from the cobs and cutting the cobs transversely in 3 cm segments. The segments are sterilized for 10 minutes in 70% ethanol and rinsed in deionized water. Ovaries are then removed and mounted for sectioning.

Specimen blocks for use in the microtome are surface sterilized in 70% ethanol for 10 minutes, and the alcohol is evaporated in a laminar flow hood. A thin layer of adhesive, "Quik Set 404" (available from Locktite Corp., Newington, Conn.), is used to immobilize the ovaries with their adiaxial surface up. The blocks with attached ovaries are placed in a Vibratome (available from Technical Products International., St. Louis, Mo.), and sectioned at a thickness of 200-400 μm. Microscopic inspection of the sections is used to identify 250 μm to 300 μm slices containing embryo sacs. Sections containing embryo sacs are collected and placed on a modified Murashige-Skoggs medium with 0.4 mg/L L-asparagine, 0.1 mg/L 6-benzylaminopurine (BAP) and 15% sucrose, pH 5.8. Media and culture conditions for plant embryos are known in the art (see e.g., Hecht et al., *Physiol. Plant* 127: 803-816 (2001), which is incorporated herein by reference).

Zygotes contained in intact embryo sacs are microinjected with ATP to promote embryo development, viability and growth. For microinjection, one to six picoliters of 200 mM ATP (available from Sigma-Aldrich, St. Louis, Mo.) is microinjected into single oocytes using a Stemi SV11 Stereomicroscope (available from Carl Zeiss Microimaging, Inc., Thornwood, N.Y.) equipped with Narishige micromanipulators and a PL-100 pico-injector (micromanipulators and injector are available from Tritech Research, Los Angeles, Calif.). Both the zygote and the central cell are microinjected with ATP and the embryo sacs are placed in culture for approximately 5 days. Embryo sacs are cultured at 25° C. in the dark on modified Murashige-Skoggs medium with 0.4 mg/L L-asparagine, 0.1 mg/L 6-benzylaminopurine (BAP) and 15% sucrose, pH 5.8. Microscopic inspection shows that without ATP microinjection approximately 44% of the embryo sacs give rise to embryos (see e.g., U.S. Pat. No. 6,300,543, Ibid.).

In order to grow plants from the microinjected zygotes, the embryo sacs are transferred to media lacking BAP, and cultured in vitro. Embryo sacs are cultured in Murashige-Skoggs medium with 0.4 mg/L L-asparagine and 10% sucrose, pH 5.8 for 5 days at 25° C. in the dark, and then transferred to the same medium containing only 3% sucrose for another 5 days. When young shoots are approximately 1.5 cm long, they are exposed to light. After the embryos have grown into plantlets in vitro, they are planted in sterilized soil or vermiculite and grown to maturity in a greenhouse. Microinjection of ATP into plant embryos may be used to improve the viability and growth of crosses between distantly related plant species (see e.g., Raghavan, *In Vitro Cell. Dev. Biol.-Plant* 39: 437-442 (2003), which is incorporated herein by reference); or to improve the viability and growth of transgenic plants (see e.g., U.S. Pat. No. 6,300,543, Ibid.).

Example 6

A Method to Provide ATP to Mature Plant Embryos to Promote Efficient Germination and Growth of Viable Seedlings A horticulturist injects mature soybean embryos with ATP using microneedles to improve the germination, viability and vigor of the soybean seeds. Soybean embryos with seed coats are injected with microneedles that penetrate the seed coat and provide ATP to the embryo including the endosperm, cotyledons and hypocotyl. Microinjected soybean seeds are sealed with a coating that prevents leakage, as well as prevents microbial contamination of the soybean embryos. Soybean seeds with optimal levels of ATP are planted in the field and tested for improved vigor.

Soybean plants (*Glycine max*) are cultivated in a greenhouse, and intact seeds at various distinct developmental stages are harvested. Soybean seeds at an early stage, middle stage and late stage of nutrient (e.g., lipids and starch) storage corresponding to approximately 80 mg, 240 mg and 400 mg per seed, respectively, are placed in the wells of a microtiter plate. Microneedles (see e.g., McAllister et al., *Proc. Natl. Acad. Sci. USA* 100: 13755-13760 (2003), which is incorporated herein by reference) approximately 30 μm in diameter and approximately 1000 μm in length are inserted into the adaxial region of the plant embryos to a penetration depth of approximately 100 to 1000 μm past the seed coat. Methods for injecting soybean seeds are known in the art (see e.g., Rolletschek et al., *New Phytologist* 167: 777-786 (2005), which is incorporated herein by reference). Soybean seeds with ATP levels greater than or equal to approximately 175 nmoles/g are optimal (see e.g., Rolletschek et al., Ibid.).

In order to achieve optimal ATP levels in the soybean embryo approximately 3 μL of 14 mM ATP solution is injected into each seed. Soybean embryo ATP levels are determined by using high performance liquid chromatography (HPLC) system with an Ultrasphere ODS 250×4.60 mm column; a Gold 125 Solvent System and and a Gold 168 diode array detector (all are available from Beckman Instruments Inc., USA). Methods to determine ATP in plant tissues are known in the art (see e.g., Liu et al., *Food Technol. Biotechnol.* 44: 531-534 (2006), which is incorporated herein by reference).

Soybean seeds with optimal ATP levels are coated with a polymer solution that prevents ATP and other metabolites from leaking out of the seed and microbial pathogens from entering the seed. Methods for coating seeds with water insoluble polymers are known in the art (see e.g., U.S. Pat. No. 3,947,996, which is incorporated herein by reference).

Soybean seeds with optimal levels of ATP are tested to assess their germination, viability and vigor. Methods to assess seed germination, viability and vigor are known in the art (see e.g., Alandadi et al., *J Food Agric. Envir.* vol. 7: 420-426 (2009), which is incorporated herein by reference). Soybean seeds that have been microinjected with ATP, as described above, are compared with control soybean seeds that have been microinjected with saline. Seeds from each group are tested in a standard laboratory germination test. Approximately 400 ATP injected seeds and 400 control seeds are placed under moist conditions on blotters or rolled towels and are maintained at 25° C. for about 7 days. At the end of this period, the seedlings are counted and characterized as normal or abnormal. The percentage germination is calculated from the number of normal seedlings, and the total number of seeds is evaluated.

Separate lots of seeds are also tested in a cold germination test: The seeds are placed under moist conditions, rolled in towels, and chilled at 10° C. for 7 days and transferred to 25° C. for 4 days. Next, the number of normal seedlings is counted, and the percentage is calculated of normal seedlings relative to the total number of seeds tested. Native soybean seeds without microinjection display cold germination percentages that range between approximately 75.25% and 85.00%. Moreover, ten normal seedlings from each lot of seed are selected at random and the lengths of the root and the primary stem are measured. In order to compare the "ATP-injected" and "saline-injected" soybean seeds, a seedling Vigor Index is calculated based on the mean lengths of the primary stems (MPSL) and roots (MPRL) of the seedlings, and the percentage germination(PG) [Vigor Index=(MPSL+MPRL)×PG]. Vigor Index values for native soybean seeds (without microinjection) range between 1105 and 1825 (see e.g., Alandadi et al., Ibid.)

In order to determine field emergence and related attributes, the seeds are sown on rows of 5meters in length with inter- and intra-row space of 50 cm and 5 cm, respectively. In each plot, 600 seeds are sown with 200 seeds in each row. Next, the number of seedlings is counted until 14 days after sowing. The percentage of seeds that emerge by 14 days after sowing is calculated. Native soybean seeds that have not been injected display field emergence percentages ranging between 31% and 41% (see e.g., Alandadi et al., Ibid.).

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A system, comprising:
   at least one computing device;
   at least one delivery device configured to receive, retain and dispense at least a portion of a composition including at least one energy supplying factor to at least one reproductive cell by way of liposomal endocytosis or electroporation, the at least one energy supplying factor including one or more of creatine, phosphocreatine, NADH, FADH$_2$ or ATP; and
   a recordable medium including one or more instructions that when executed on the computing device cause the computing device to regulate dispensing of at least a portion of the composition; wherein the at least one computing device includes at least one computing device located on or in the at least one delivery device.

2. The system of claim 1, wherein the at least one delivery device includes at least one implantable delivery device.

3. The system of claim 1, wherein the at least one computing device includes at least one computing device located remotely from the at least one delivery device.

4. The system of claim 1, wherein the at least one computing device includes one or more of a desktop computer, workstation computer, or computing system.

5. The system of claim 1, wherein the at least one computing system includes one or more of a cluster of processors, networked computer, tablet personal computer, laptop computer, mobile device, mobile telephone, or personal digital assistant computer.

6. The system of claim 1, further comprising one or more instructions that when executed on the at least one computing device cause the at least one computing device to generate at least one output to a user.

7. The system of claim 6, wherein the at least one output includes at least one graphical illustration of one or more of the composition, at least one reproductive cell or substance associated with the composition, at least one property of the delivery device; or at least one property of dispensing the at least one delivery device.

8. The system of claim 6, wherein the at least one output includes at least one protocol for making the composition.

9. The system of claim 6, wherein the at least one output includes at least one protocol for administering the composition to the at least one reproductive cell.

10. The system of claim 6, wherein the user includes at least one entity.

11. The system of claim 10, wherein the entity includes at least one person, or computer.

12. The system of claim 6, wherein the output includes output to a user readable display.

13. The system of claim 12, wherein the user readable display includes a human readable display.

14. The system of claim 12, wherein the user readable display includes one or more active displays.

15. The system of claim 12, wherein the user readable display includes one or more passive displays.

16. The system of claim 12, wherein the user readable display includes one or more of a numeric format, graphical format, or audio format.

17. The system of claim 1, further comprising one or more instructions for determining one or more parameters for selecting the at least one reproductive cell from other reproductive cells.

18. The system of claim 1, further comprising one or more instructions for determining one or more parameters for administering the composition to at least one reproductive cell.

19. The system of claim 1, further comprising one or more instructions for receiving information related to one or more reproductive cell indicators prior to, during, or subsequent to administering the composition to the at least one reproductive cell.

20. The system of claim 19, wherein the information related to one or more reproductive cell indicators includes information from at least one of an assay, image, or gross assessment of the at least one reproductive cell or reproductive cell related tissue prior to, during, or subsequent to administering the composition.

21. The system of claim 20, wherein the assay includes at least one technique including spectroscopy, microscopy, electrochemical detection, polynucleotide detection, histological examination, biopsy analysis, fluorescence resonance energy transfer, electron transfer, enzyme assay, electrical conductivity, isoelectric focusing, chromatography, immunoprecipitation, immunoseparation, aptamer binding, filtration, electrophoresis, immunoassay, or radioactive assay.

22. The system of claim 20, wherein the at least one image includes one or more images acquired by at least one of laser, holography, x-ray crystallography, optical coherence tomography, computer-assisted tomography scan, computed tomography, magnetic resonance imaging, positron-emission tomography scan, ultrasound, x-ray, electrical-impedance monitoring, microscopy, spectrometry, flow cytometry, radioisotope imaging, thermal imaging, infrared visualization, multiphoton calcium-imaging, photography, or in silico generation.

23. The system of claim 1, wherein the at least one reproductive cell is located in at least one of in situ, in vitro, in vivo, in utero, in planta, in silico, or ex vivo.

24. The system of claim 1, wherein the at least one reproductive cell is located in at least one subject.

25. The system of claim 24, wherein the at least one subject includes at least one of an invertebrate or vertebrate animal.

26. The system of claim 24, wherein the at least one subject includes at least one of a reptile, mammal, amphibian, bird, or fish.

27. The system of claim 24, wherein the at least one subject includes at least one human.

28. A system, comprising:
   at least one computing device;
   at least one delivery device configured to receive, retain and dispense at least a portion of a composition including at least one energy supplying factor to at least one reproductive cell by way of liposomal endocytosis or electroporation, the at least one energy supplying factor including one or more of creatine, phosphocreatine, NADH, FADH$_2$, or ATP; and
   a recordable medium including one or more instructions that when executed on the computing device cause the computing device to regulate dispensing of at least a portion of the composition;
   wherein the at least one reproductive cell is located in at least one subject.

29. The system of claim 28, wherein the at least one delivery device includes at least one implantable delivery device.

30. The system of claim 28, wherein the at least one computing device includes at least one computing device located remotely from the at least one delivery device.

31. The system of claim 28, wherein the at least one computing device includes one or more of a desktop computer, workstation computer, or computing system.

32. The system of claim 28, wherein the at least one computing system includes one or more of a cluster of processors, networked computer, tablet personal computer, laptop computer, mobile device, mobile telephone, or personal digital assistant computer.

33. The system of claim 28, further comprising one or more instructions that when executed on the at least one computing device cause the at least one computing device to generate at least one output to a user.

34. The system of claim 33, wherein the at least one output includes at least one graphical illustration of one or more of the composition, at least one reproductive cell or substance associated with the composition, at least one property of the delivery device; or at least one property of dispensing the at least one delivery device.

35. The system of claim 33, wherein the at least one output includes at least one protocol for making the composition.

36. The system of claim 33, wherein the at least one output includes at least one protocol for administering the composition to the at least one reproductive cell.

37. The system of claim 33, wherein the user includes at least one entity.

38. The system of claim 37, wherein the entity includes at least one person, or computer.

39. The system of claim 28, wherein the output includes output to a user readable display.

40. The system of claim 39, wherein the user readable display includes a human readable display.

41. The system of claim 39, wherein the user readable display includes one or more active displays.

42. The system of claim 39, wherein the user readable display includes one or more passive displays.

43. The system of claim 39, wherein the user readable display includes one or more of a numeric format, graphical format, or audio format.

44. The system of claim 28, further comprising one or more instructions for determining one or more parameters for selecting the at least one reproductive cell from other reproductive cells.

45. The system of claim 28, further comprising one or more instructions for determining one or more parameters for administering the composition to at least one reproductive cell.

46. The system of claim 28, further comprising one or more instructions for receiving information related to one or more reproductive cell indicators prior to, during, or subsequent to administering the composition to the at least one reproductive cell.

47. The system of claim 46, wherein the information related to one or more reproductive cell indicators includes information from at least one of an assay, image, or gross assessment of the at least one reproductive cell or reproductive cell related tissue prior to, during, or subsequent to administering the composition.

48. The system of claim 47, wherein the assay includes at least one technique including spectroscopy, microscopy, electrochemical detection, polynucleotide detection, histological examination, biopsy analysis, fluorescence resonance energy transfer, electron transfer, enzyme assay, electrical conductivity, isoelectric focusing, chromatography, immunoprecipitation, immunoseparation, aptamer binding, filtration, electrophoresis, immunoassay, or radioactive assay.

49. The system of claim 28, wherein the at least one reproductive cell is located in at least one of in situ, in vitro, in vivo, in utero, in silico, or ex vivo.

* * * * *